US010201185B2

(12) United States Patent
Bleloch et al.

(10) Patent No.: US 10,201,185 B2
(45) Date of Patent: Feb. 12, 2019

(54) VAPORIZER DEVICE

(71) Applicant: Loto Labs, Inc., Redwood City, CA (US)

(72) Inventors: Andrew L. Bleloch, Redwood City, CA (US); Neeraj S. Bhardwaj, Redwood City, CA (US); Gabriel Brown, Palo Alto, CA (US)

(73) Assignee: Loto Labs, Inc., Belmont, CA (US)

( * ) Notice: Subject to any disclaimer, the term of this patent is extended or adjusted under 35 U.S.C. 154(b) by 514 days.

(21) Appl. No.: 14/710,136

(22) Filed: May 12, 2015

(65) Prior Publication Data

US 2015/0320116 A1 Nov. 12, 2015

Related U.S. Application Data

(60) Provisional application No. 61/991,757, filed on May 12, 2014.

(51) Int. Cl.
A24F 47/00 (2006.01)
A61M 11/04 (2006.01)
(Continued)

(52) U.S. Cl.
CPC ......... *A24F 47/008* (2013.01); *A61M 11/042* (2014.02); *A61M 15/06* (2013.01); *F22B 1/281* (2013.01); *H05B 6/06* (2013.01); *H05B 6/108* (2013.01); *A61L 9/037* (2013.01); *A61M 2205/3368* (2013.01);
(Continued)

(58) Field of Classification Search
CPC ..... A24F 47/008; A61L 9/037; A61M 11/042; A61M 15/06; A61M 2205/3368; A61M 2205/3375; A61M 2205/3569; A61M 2205/3592; A61M 2205/50; A61M 2205/505; A61M 2205/584;
(Continued)

(56) References Cited

U.S. PATENT DOCUMENTS 5,613,505 A 3/1997 Campbell et al.
5,934,289 A 8/1999 Watkins et al.
(Continued)

FOREIGN PATENT DOCUMENTS

CN 203748673 U 8/2014
EP 2113178 A1 11/2009
(Continued)

OTHER PUBLICATIONS

Williams, Monique, et al. "Metal and silicate particles including nanoparticles are present in electronic cigarette cartomizer fluid and aerosol." PloS one 8.3 (2013): e57987.
(Continued)

*Primary Examiner* — Dana Ross
*Assistant Examiner* — Joe E Mills, Jr.
(74) *Attorney, Agent, or Firm* — The Webb Law Firm

(57) ABSTRACT

A vaporizer device includes a cartridge configured to hold a vaporizable substance, a wick element coupled to the cartridge, where the wick element is configured to contact the vaporizable substance located in the cartridge and an induction heating element inductively coupled to the wick element, where the wick element is configured to heat the vaporizable substance based on induction heating of the wick element by the induction heating element.

21 Claims, 14 Drawing Sheets

(51) Int. Cl.
*F22B 1/28* (2006.01)
*H05B 6/06* (2006.01)
*H05B 6/10* (2006.01)
*A61M 15/06* (2006.01)
*A61L 9/03* (2006.01)

(52) U.S. Cl.
CPC ............... *A61M 2205/3375* (2013.01); *A61M 2205/3569* (2013.01); *A61M 2205/3592* (2013.01); *A61M 2205/50* (2013.01); *A61M 2205/505* (2013.01); *A61M 2205/584* (2013.01); *A61M 2205/8206* (2013.01)

(58) Field of Classification Search
CPC . A61M 2205/8206; H05B 6/06; H05B 6/108; H05B 6/1081; H05B 6/105; H05B 6/0244
USPC .......................................... 219/628, 635, 667
See application file for complete search history.

(56) References Cited

U.S. PATENT DOCUMENTS

| | | | |
|---|---|---|---|
| 6,053,176 A | 4/2000 | Adams et al. | |
| 6,803,550 B2 | 10/2004 | Sharpe et al. | |
| 6,994,096 B2 | 2/2006 | Rostami et al. | |
| 7,878,209 B2 | 2/2011 | Newbery et al. | |
| 8,375,957 B2 | 2/2013 | Hon | |
| 8,393,331 B2 | 3/2013 | Hon | |
| 8,689,805 B2 | 4/2014 | Hon | |
| 8,881,737 B2 | 11/2014 | Collett et al. | |
| 8,910,640 B2 | 12/2014 | Sears et al. | |
| 2002/0078956 A1* | 6/2002 | Sharpe | A61M 11/042 128/203.26 |
| 2003/0230567 A1* | 12/2003 | Centanni | A61L 2/07 219/628 |
| 2004/0149297 A1 | 8/2004 | Sharpe | |
| 2006/0219962 A1* | 10/2006 | Dancs | A01M 1/2077 250/577 |
| 2009/0272379 A1 | 11/2009 | Thorens et al. | |
| 2009/0299328 A1* | 12/2009 | Mudd | A61M 5/19 604/506 |
| 2010/0024834 A1 | 2/2010 | Oglesby et al. | |
| 2011/0226236 A1* | 9/2011 | Buchberger | A61M 11/041 128/200.23 |
| 2011/0309157 A1 | 12/2011 | Yang et al. | |
| 2012/0109687 A1* | 5/2012 | Tubb | A61B 5/14532 705/3 |
| 2012/0234315 A1* | 9/2012 | Li | A24F 47/008 128/200.21 |
| 2013/0081642 A1 | 4/2013 | Safari | |
| 2013/0087160 A1 | 4/2013 | Gherghe | |
| 2013/0199528 A1* | 8/2013 | Goodman | F22B 1/282 128/203.26 |
| 2013/0306065 A1 | 11/2013 | Thorens et al. | |
| 2013/0340750 A1* | 12/2013 | Thorens | A24F 47/008 128/202.21 |
| 2014/0205272 A1* | 7/2014 | Midgette | A61L 9/037 392/395 |
| 2014/0238424 A1* | 8/2014 | Macko | A24F 47/008 131/328 |
| 2014/0270729 A1* | 9/2014 | DePiano | A24F 47/008 392/397 |
| 2014/0305449 A1 | 10/2014 | Plojoux et al. | |
| 2014/0321837 A1* | 10/2014 | Flick | F24H 1/0018 392/387 |
| 2014/0334802 A1* | 11/2014 | Dubief | A61L 9/03 392/390 |
| 2014/0346689 A1* | 11/2014 | Dubief | A24F 47/008 261/142 |
| 2014/0353856 A1* | 12/2014 | Dubief | A24D 3/041 261/128 |
| 2015/0181937 A1* | 7/2015 | Dubief | A24F 47/008 131/329 |

FOREIGN PATENT DOCUMENTS

| | | | |
|---|---|---|---|
| EP | 2460424 A1 | 6/2012 | |
| WO | WO 2013/159245 A1 | 10/2013 | |
| WO | WO 2014/071329 A1 | 5/2014 | |

OTHER PUBLICATIONS

Brown, Christopher J., and James M. Cheng. "Electronic cigarettes: product characterisation and design considerations." Tobacco control 23.suppl 2 (2014): ii4-ii10.
Famele, Marco, et al. "The Chemical Components of Electronic Cigarette Cartridges and Refill Fluids: Review of Analytical Methods." Nicotine & Tobacco Research (2014): ntu197.
Yaeger, Brian. "Induction Heating. The vaporizer of the future" (2014).
International Search Report and Written Opinion for PCT/US2015/030427 dated Aug. 28, 2015 (13 pages).

\* cited by examiner

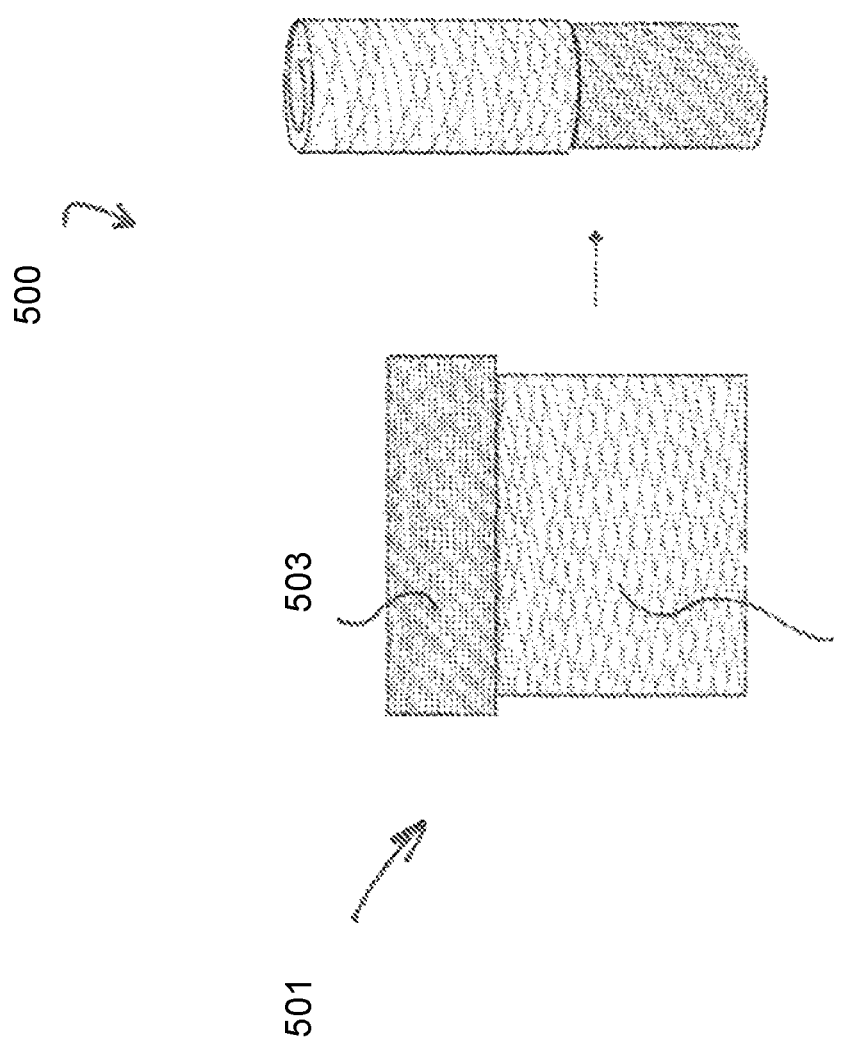

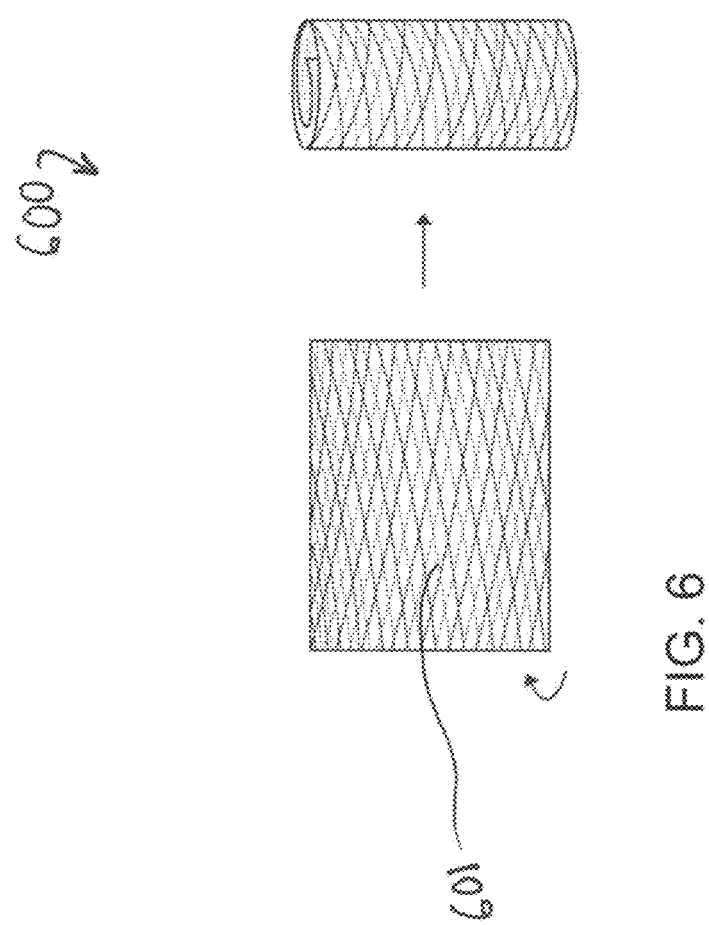

VAPORIZER DEVICE

RELATED APPLICATIONS

This application claims the benefit, under 35 USC § 119(e), of U.S. Provisional Application No. 61/991,757 filed May 12, 2014 entitled "Improved Vaporizer", the entirety of which is incorporated herein by reference.

FIELD OF THE INVENTION

The present disclosure relates generally to what are called e-cigarettes, vaporizers, or "vapes" in common parlance. These are devices that produce an aerosol of a material to be inhaled. The present disclosure relates more particularly to the use of induction heating to produce an aerosol.

BACKGROUND

To vaporize liquids, such as e-liquids (nicotine-containing, sometimes-flavored liquids used in e-cigarettes as replacements for cigarettes) and liquids containing herbal extracts, for inhalation by a user, the liquid must be raised to a suitable temperature while the user draws air past the heated liquid. The current prevalent technology consists of a reservoir of liquid from which a wick, typically made from glass fiber or stainless steel mesh, wicks the liquid into a heating coil, typically made from the FeCrAl alloy Kanthal, which is heated by passing a current through the coil.

The current approach suffers from several disadvantages. First, the temperature of the heater coil is necessarily higher than the temperature ideally required to vaporize liquid in the wick. This temperature difference can result in unwanted chemical reactions taking place at this hotter surface of the heater coil when sufficient heat is available to achieve the desired vaporization of liquid in the bulk of the wick. The unwanted chemical reactions can detrimentally effect both the quality of the experience by influencing the flavor and the health impact by increasing the presence of toxic chemicals. Second, the proximity of the coil to the liquid means any electrical conductivity of the liquid effects the functioning of the vaporizer. Third, the practical design of the reservoir and wick often results in leaks. Thus, there is a need for an improved vaporizer device.

SUMMARY

This present disclosure provides systems and methods designed and configured to apply induction-heating in a vaporizer device to reduce the range of temperatures in contact with a liquid at the time of vaporization, designed and configured to separate the electrical paths from the air and liquid, and designed and configured to provide precise and rapid control of heating.

Disclosed herein is a vaporizer device that comprises a combined wick and heating element where the wick is inductively heated. Among other advantages, using induction heating allows the heat to be more evenly distributed through the volume of the liquid to be vaporized and thus to achieve the same or better rates of vapor production with lower temperature gradients and hence lower peak temperatures or hot spots.

Wicking is a process of moving liquids by the action of surface tension. The underlying physical process is similar for capillary action. For the wick to draw up the liquid so that it may be simultaneously heated and exposed to an air path to be drawn out as an aersol mist, which may also be called a vapor, the wick may be a finely divided solid material. The wicking or capillary action relies on a reduction in the surface energy of the two separate surfaces—the liquid surface and the solid surface—when compared to the two surfaces in contact. The wicking or capillary action includes an effect that depends on the radius of curvature of both the liquid surface and the solid surface and hence there may be a need for large surface areas and small radii of curvature both of which are achieved by a finely divided material. The radius of curvature of the solid surface is important since as the liquid wets the solid, conformation of the liquid surface is largely determined by the solid. Another way of expressing the reduction in energy when the two materials are in contact vs. separate, is that the contact angle of a drop of the liquid placed on a flat surface of the wick material must be less than 90 degrees. As an example, when a capillary is placed in liquid mercury, the contact angle is greater than 90 degrees and the liquid level goes down, not up, which is the reverse of wicking.

With this in mind, in one embodiment a combination wick and inductively heated element may be constructed of one material that performs both functions of wicking and heating. An alternating current of an appropriate frequency in the induction coil induces eddy currents and/or magnetic hysteresis heating of the wick element, causing the wick element to heat up. The wick material itself is a source of heat to the vaporizable substance rather than being indirectly heated by a resistively heated coil as in some current e-cigarette designs. According to embodiments, the material of the wick element may have the following properties: a sufficiently small contact angle with a liquid to be vaporized; be susceptible to induction heating so that the required temperature may be reached; and be finely divided enough to transport the liquid within the wick material and when the liquid is heated, create a vapor that is satisfying to the user.

According to embodiments, a vaporizer device as disclosed herein may have two modes of operation. One mode of operation is to heat loose leaf material where the induction heating element acts as a simple heater. In the other mode of operation the induction heating element, which acts as an absorber according to a wicking action, operates to vaporize waxes or liquids. The latter mode of operation is a combination of induction heating and wicking where one structure provides the wicking action and the heating simultaneously. In one embodiment, the induction heating element is a mesh of one material that fulfills both functions but the induction heating element may also be formed of more than one material and is a more intimate mixture of materials than simply wrapping a heating coil around a wick.

A vaporizer device as disclosed herein may have the ability to vaporize a number of different materials. An example of such a material is what has been referred to as "e-liquid", which consists of varying proportions of propylene glycol and glycerine, and may or may not contain nicotine and flavors. For some people these devices can be a healthier replacement for smoking cigarettes. According to embodiments, a vaporizer device as disclosed herein may have the ability to vaporize a number of different materials from the same device with or without a simple exchange of a coil and the material to be vaped itself. Thus one device may be capable of vaping dry leaf material, waxes and e-liquids in the same device.

According to embodiments, a vaporizer device as disclosed herein may have the use of exchangeable cartridges that are self contained with the vaping material, also called a vaporizable substance, and an induction wick element. Such cartridges may also be encoded with information that allows the device to sense information that allows the vaping conditions to be set specifically for that material. Induction provides a unique opportunity to use these self-contained cartridges by separating the heating from electrical contact. Accordingly, where the wick element is located in a cartridge, there is no need for electrical connections to a power source since the wick element is heated via induction and the cartridge is independent of the electronic components that require a power source such as a battery.

According to embodiments, a vaporizer device as disclosed herein may have a microprocessor on the device. Accordingly, the vaporizer device may have the ability to precisely control heating of the vaporizable substance. Further, according to embodiments, feedback information, such as pressure of the vapor exiting/entering the device and/or temperature of the heating component, may be used to optimize the vaping experience for a user. The use of feedback information may give the same experience for a user as the user inhales, puff after puff, irrespective of the recent history. In one embodiment, a heating pulse shape, according to temperature versus time, at heater of the vaporizer device may start at a high power to get up to temperature but then reduces to an optimal power before the temperature overshoots. This can reduce the need to have the heating element at an idle state while the device is in active use. In one embodiment, a heater of the vaporizer device may be controlled by the processor according to a control loop function. In another embodiment, the induction heating element of the vaporizer device may be controlled by the processor according to a predictive operation. In a predictive operation, instead of using a direct feedback of the temperature to adjust the power to maintain that temperature of the heater, a calculation may be performed based on a current temperature and a predetermined model of the behavior. A power level is then set that will achieve close to a desired temperature without the requirement for tracking it in real time. Accordingly, the power needed for each inhalation is determined and the processor controls the heater to use that amount of power.

Advantages of the present disclosure include:

Even heating, and therefore a smaller range of temperatures, so the hottest spots are not much hotter than the bulk of the vaping volume;

Separation of the wick element, the vaporizable material, and the container that holds the vaporizable material from all the other components of the vaporizer.

No direct electrical connections that are exposed to the vapor produced by the vaporizable substance. This allows the wick material to be separated from the rest of the electronics and enables a number of further advantages:

the ability to change flavors or even vaporizable substances, for example, from nicotine containing substances to medical marijuana containing substances (where medical marijuana is legal);

it is easier to prevent leaking because electrical connections do not need to feed through to the wick material;

a range of materials that the vapor is exposed to can be limited to the vial, the wick material, and the vaporizable substance itself so as to remove or reduce unwanted catalytic reactions or unwanted species in the vapor. No other material need be in a vapor path of the device.

Precise control of the heating cycle.

FIGURES

Various features of the embodiments described herein are set forth with particularity in the appended claims. The various embodiments, however, both as to organization and methods of operation, together with advantages thereof, may be understood in accordance with the following description taken in conjunction with the accompanying drawings as follows.

FIG. 5 is another embodiment of a wick element of a vaporizer device according to the present disclosure.

FIG. 6 is another embodiment of a wick element of a vaporizer device according to the present disclosure.

DETAILED DESCRIPTION

Various embodiments are directed to devices, apparatuses, systems, and methods for the vaporizing materials for inhalation by a human being. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

As disclosed herein a vaporizer or vaporizer device includes such devices as electronic cigarettes (e-cig or e-cigarette), personal vaporizers (PV), electronic nicotine delivery systems (ENDS), and similar devices that produce an effect that is much like smoking tobacco. As discussed herein an induction heating system comprises a susceptor material, which is the material to be heated by the induction process, and an induction coil which generates a magnetic field to induce eddy currents in the susceptor material when the induction coil is powered. A coil is a practical geometry for the use in induction heating. While any AC magnetic field (i.e. around any conductor anywhere carrying AC) will cause some inductive heating, a coil geometry makes efficient use of that field. In embodiments described herein, an induction coil may have a cylindrical shape. In additional embodiments, the induction coil is not cylindrical, but instead has a square or spherical shape in implementation.

Figure 1:
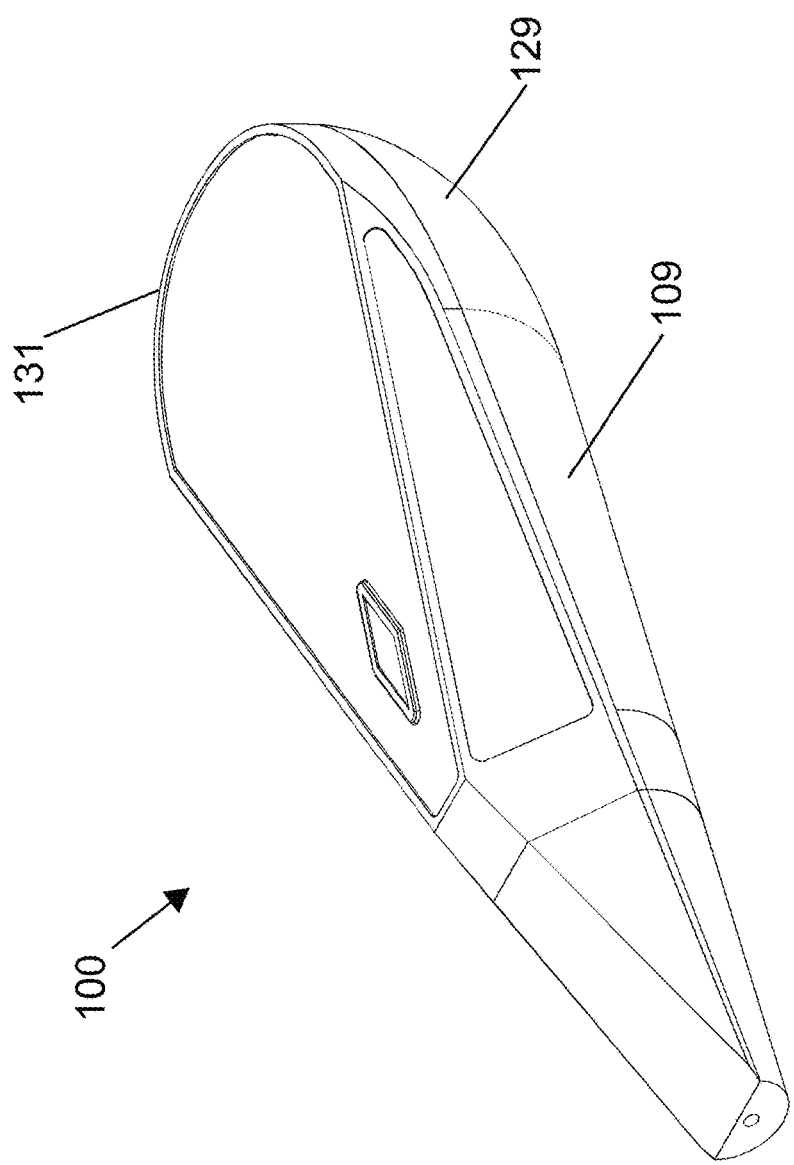
FIG. 1 is an embodiment of a vaporizer device according to the present disclosure.
Figure 2:
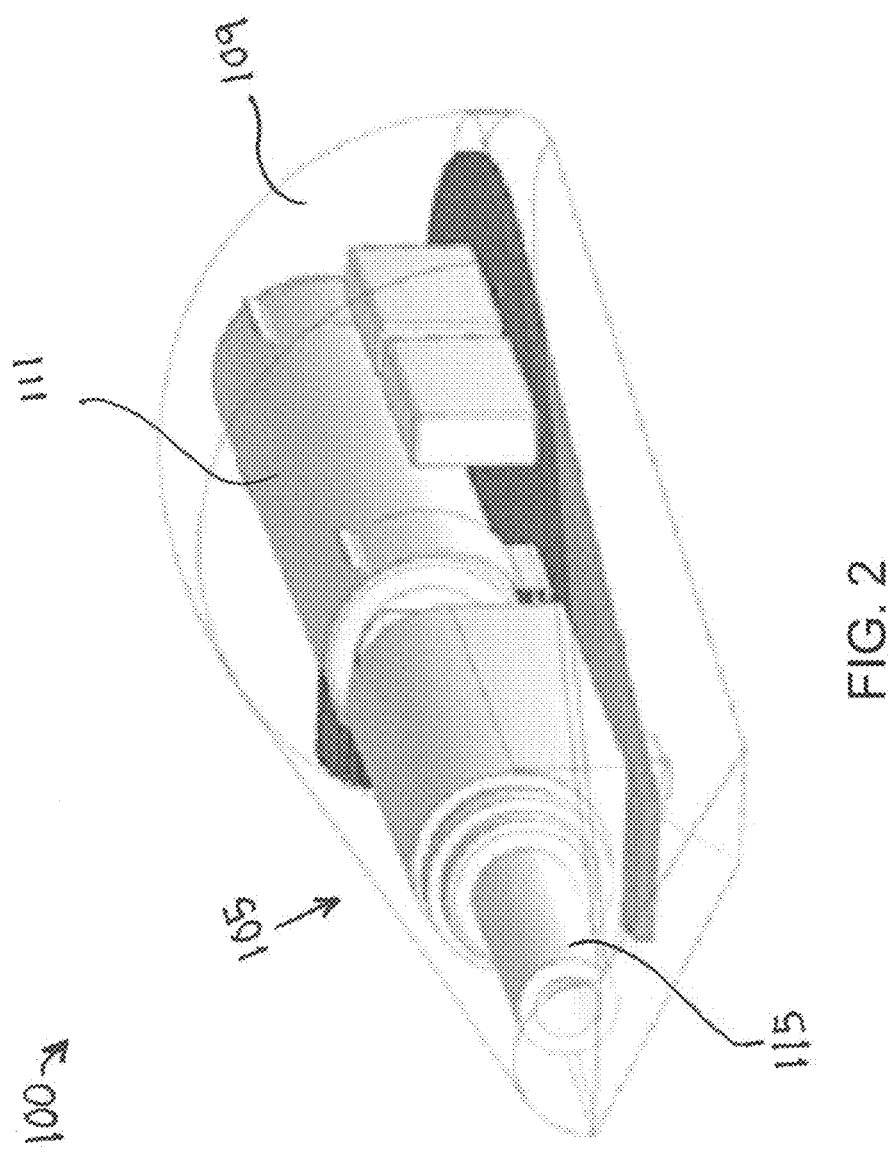
FIG. 2 is an assembled view of a vaporizer device according to the present disclosure.
Figure 3:
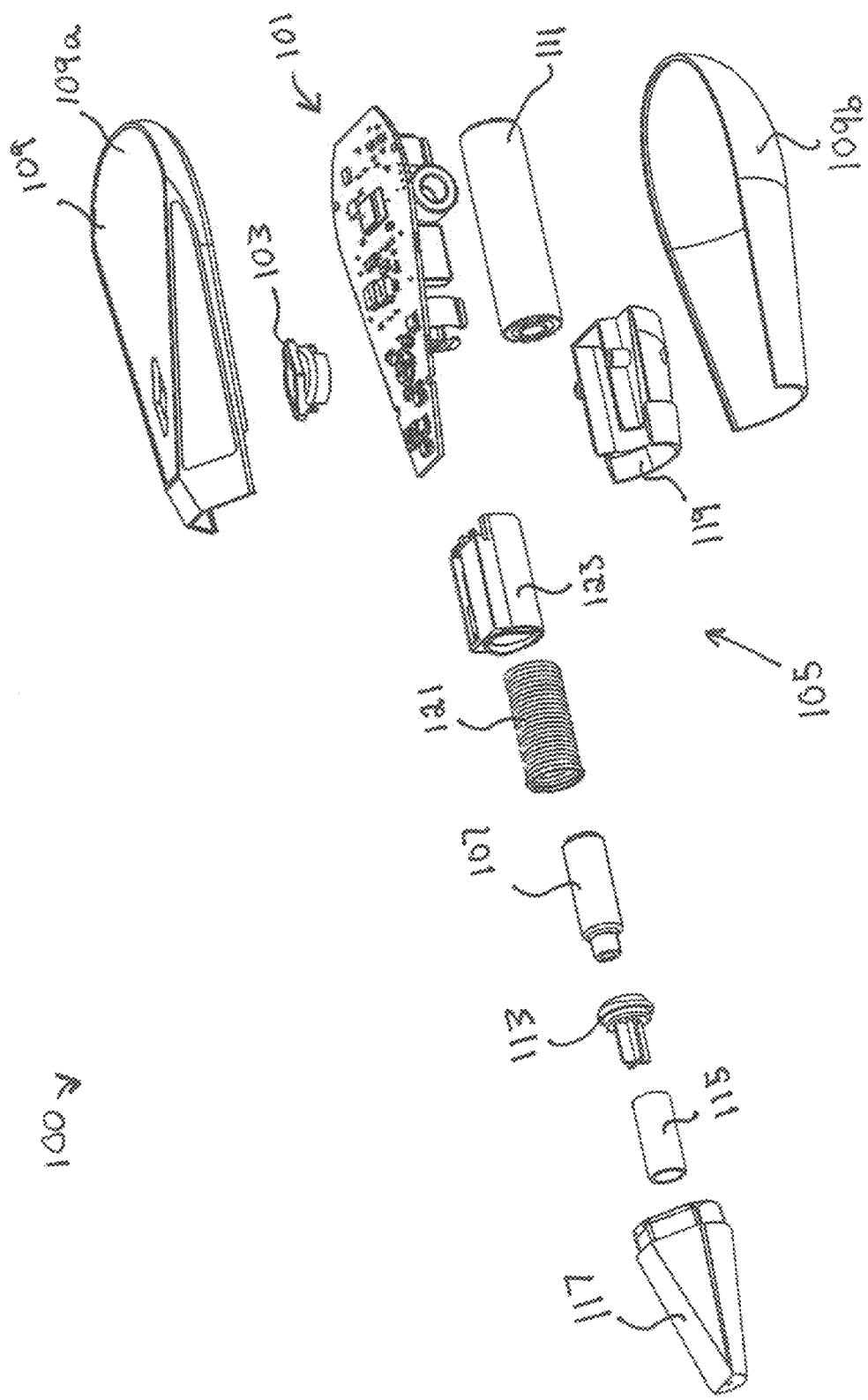
FIG. 3 is a disassembled view of a vaporizer device according to the present disclosure.

FIGS. 1 and 2 show assembled views of a vaporizer device 100, and FIG. 3 shows a disassembled view of the vaporizer device 100, according to the present disclosure. FIG. 2 illustrates the vaporizer device 100 with the housing 109 being transparent. As shown in FIG. 3, the vaporizer device 100 comprises electronic control components 101, at least one activation button 103, an induction element assembly 105, a cartridge 107, a housing 109, a power source 111, a valve 113, a tube 115, and a mouthpiece component 117.

The induction element assembly 105 comprises an internal frame or chassis 119, an induction heating element 121, such as an induction coil, and a heating element body 123. As shown in the embodiment of FIG. 2, the heating element body 123 is sized and configured to hold the induction coil 121 when it is disposed within the heating element body 123. The internal chassis 119 is sized and configured to hold the induction coil 121 and heating element body 123 in proximity to the electronic control components 101, which allows for compact size and control of the induction coil 121 with the electronic control components 101. Additionally, the heating element body 123 may act as an insulator to the heat generated by induction heating of a wick element within the cartridge 107 and also shields electronic components from electromagnetic radiation generated by the induction coil 121.

The cartridge 107 is sized and configured to fit within the induction coil 121, which allows for compact construction of the vaporizer device 100. The cartridge 107 has an aperture 125 in one end that allows the vapor or aerosol from the vaporizable substance to flow out of the cartridge 107. In embodiments, the cartridge is configured with a reservoir and the reservoir is structured to hold a vaporizable substance. A wick element is configured to be contained within the reservoir and the wick element contacts the vaporizable substance of the reservoir, the wick element is described in detail with regard to FIGS. 4a-6 below. The induction coil 121 is configured to be housed within the heating element body 123. The induction coil 121 is inductively coupled to a wick element within the cartridge 107 such that the wick element is heated by electromagnetic induction, through heat generated in the wick element by eddy currents.

Additionally, in embodiments, the cartridge 107 may be a replaceable and/or disposable container for the vaporizer device. In one embodiment, the cartridge may contain a predetermined amount of a vaporizable substance and when the vaporizable is used up or near to be used up, a user may replace with the cartridge. The vaporizable substance may be any composition, material, or matter that produces a vapor for inhalation by a human being when heated to a predetermined temperature. In one embodiment, the vaporizer device may comprise an indicator of the amount of vaporizable substance remaining in a cartridge. The indicator may be located on the cartridge or on the housing of the vaporizer device. The indicator may include a digital or analog output screen located on the vaporizer device that is visible to a user.

Furthermore, the vaporizable device may have a second indicator that indicates when the cartridge is close to empty and acts as a low volume indicator for the vaporizable substance. Additionally, in one embodiment, the cartridge may be configured to be refilled with a vaporizable substance. Further, the cartridge may be configured to be refilled while located within the vaporizer device such as through a vent or aperture in the housing. Additionally, in embodiments, an induction coil may be formed as part of a replaceable cartridge such that a cartridge structure (the cartridge body, the wick element, and the induction coil) is designed to be replaced. Such a replaceable cartridge would include electrical connections to connect the induction coil to other electronic control components.

In one embodiment, replacement of the cartridge may be accomplished by removing the housing and separating any additional components as necessary. In another embodiment, removal of the housing may not necessary. In one embodiment, the vaporizable device may allow a user to remove an empty cartridge and to replace it with a new, full cartridge within the induction element assembly without removing any components. In one embodiment, the vaporizer device may comprise a channel or chamber defined therein that allows for removal of an empty or near empty cartridge and accepts a replacement cartridge. In another embodiment, the vaporizer device comprises a chamber or channel that folds, twits, or is otherwise manipulated open to accept a new cartridge and then is manipulated to close and place the cartridge in the appropriate position to enable heating of the vaporizable substance within the cartridge. In another embodiment, the housing may have a chamber or channel defined therein and the housing is configured to receive the cartridge within the chamber or channel.

In addition, in embodiments where the wick element is located within the cartridge, there is no need for electrical connections to a power source since the wick element is heated via induction. Additionally, the cartridge may comprise a body having an inside surface and the wick element may be positioned adjacent to the inside surface of the cartridge. The neck or body of the cartridge may act as an insulating member between the wick element and the induction heating element. The insulating member removes the induction coil from contact with the vaporizable substance in the cartridge, such as a liquid. The cartridge may be made of an appropriate insulating material such as glass, fiberglass, ceramic, etc. According to embodiments, the open end of the cartridge defines an air path through the vaporizer device.

According to embodiment shown in FIG. 3, the activation button 103 may be configured to protrude through an aperture 127 in the housing 109 so that a user may activate the device 100. In other embodiments, the activation button 103 may be configured such that a depression of a physical button is not necessary, for example, the activation button 103 may comprise a touchscreen component, such as a capacitive touchscreen. This allows for a user to work with the vaporizer device 100 to verify information such as age, number of uses, and other analytics. This capability combined with onboard sensors creates a smart vaporizer capable of being connected for communication and networked to local computers or the internet.

In addition, in another embodiment, the activation button 103 may be integrated with another aspect of the vaporizer device 100. For instance, the activation button 103 may be integrated with the mouthpiece component 117 such that, contact with a user's mouth to the mouthpiece component 117 may allow for activation of the vaporizer device 100. In addition, the activation button 103 may comprise a fingerprint scanner, or other form of identification device for a user, so that a user may personalize their own device and prevent others from using the device. This may be helpful in situations where monitoring of a vaporizer device is not always available and thus prevents another unauthorized user, such as child, from using the device.

The housing 109 is sized and configured to substantially house, or enclose, the components of the vaporizer device 100, to provide an external appearance to the device, and is shaped to fit ergonomically in the hand of a user. According to the embodiment shown in FIG. 3, the housing 109 comprises an upper housing 109a and a lower housing 109b. The upper and lower housing 109a, 109b may be structured with an aesthetically pleasing appearance, such as to mimic the appearance of a wood grain, and may comprise colors, shapes, indicia as desired. In addition, the upper and lower housing 109a, 109b may be replaceable to allow for a user to customize a particular appearance of the vaporizer device 100.

The housing 109 may be made from any suitable material such as wood, metal, fiberglass, plastic, etc. In the embodiment shown in FIG. 1, the housing 109 comprises curved wooden accents 129 leading to metal edges 131 so that the vaporizer device 100 will not roll off a flat surface, such as a table in this configuration as opposed to many existing vaporizers. Wood may be desirable as a material for the housing since it is organic, a good insulator, and aesthetically pleasing. The mouthpiece component 117 can be interchangeable and variants may be designed such that the mouthpiece component 117 restricts airflow to reproduce the pulling sensation that users may prefer when it comes to smoking regular cigarettes, cigars, and pipes. The activation button 103 may comprise one or more control buttons, sensors, or switches that allow a user to interact with the vaporizer device 100. The simplest interaction of the activation being turning the device on and off.

According to the present disclosure, a wick element is configured to heat substances that are adjacent or in contact with the material of the wick element. Therefore, a vaporizable substance may be heated based on induction heating of the wick element by the induction heating element. According to embodiments, the wick element may also be configured to transfer a vaporizable substance from the reservoir based on a capillary action of the wick element. In embodiments where the vaporizable substance is a liquid or viscous substance, as the liquid is vaporized, more liquid moves up the wick element.

The configuration of the wick element may be a stranded wire, a stranded rope of material, a mesh, a mesh tube, several concentric mesh tubes, a cloth, sheets of material, or a foam (or other porous solid) with sufficient porosity, a roll of fine metal mesh or some other arrangement of metal foil, fibers or mesh, or any other geometry that is appropriately sized and configured to carry out the wicking action as described herein. The wick element may further comprises fins, protrusions, or other details that are configured to hold a solid or semi sold material in contact with the wick element.

The wick element may also be constructed of a combination of materials to achieve an appropriate effect. In one embodiment, the wick element is an interwoven cloth, or otherwise intimately mixed combination, of fine induction heating wires, strands, or threads with wicking wires, strands, or threads. In addition to a cloth or mesh configuration, the materials of the wick element may be combined in the form of a rope or foam, or suitably deployed thin sheets of material. In one embodiment, the wick element comprises rolled up alternating foils of material. The wick element is partially or completely surrounded by the induction coil that is not necessarily in contact with the mesh. As the wick element may be formed from a mesh, the mesh wick may be made of a material that is efficiently heated by induction such as a FeCrAl alloy. In one embodiment, the mesh wick may be formed using a Kanthal mesh. Additionally, the wick element may be removable from a cartridge so that the wick element is able to be cleaned and reused or replaced separate from the cartridge.

The materials used in the wick element may comprise a magnetic material or a metallic conductor. Further, the wick element may comprise materials that produce heat eddy currents or magnetic hysteresis when the wick element is exposed to an electromagnetic field. For example, magnetic or metallic conductor materials that have considerable hysteresis in the range of electromagnetic fields may be employed with the vaporizer device. In one embodiment, the wick element is comprised of a material such that heating is carried out both by eddy currents and also by movement of the magnetic domain walls. In one embodiment, the wick element material is iron. In another embodiment, the wick element comprises ceramic magnets, such as ferrite. In still another embodiment, the wick element comprises metallic conductors that heat by eddy currents. In yet another embodiment, the wick element comprises a semiconductor.

Figure 4B:
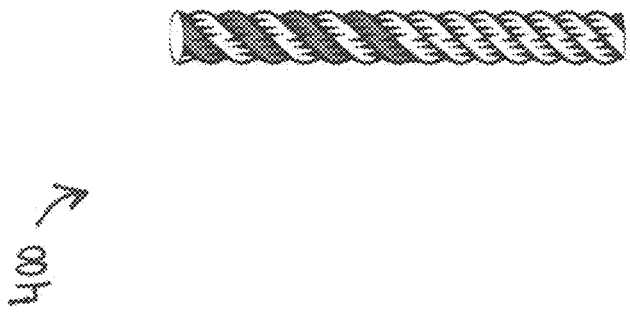
FIG. 4b is another embodiment of a wick element of a vaporizer device according to the present disclosure.
Figure 4A:
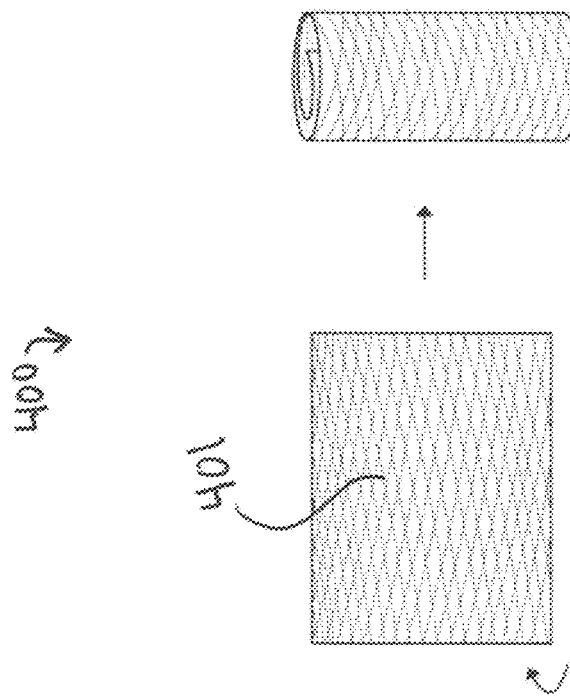
FIG. 4a is an embodiment of a wick element of a vaporizer device according to the present disclosure.

FIG. 4a displays a wick element 401 that comprises an induction energy absorbing mesh 401 configured to both wick and heat effectively, where the mesh 401 is fashioned into a spiral or tube and is designed to be placed into the cartridge. As shown in the embodiment of FIG. 4a, the mesh 401 is shown with the warp and weft of the mesh 401 on a diagonal. In another embodiment, the warp and weft are parallel or perpendicular to the axis of the wick. In FIG. 4b, the wick element 402 is made of stainless steel wire wound up in the form of a rope. In one embodiment, some of the strands of the wick element may be replaced with a magnetic material such as Kanthal. Additionally, according to embodiments of the wick elements 401, 402 may include additional heat conducting elements attached to the wick element, such as protrusions in the form of heat conducting fins, or a tube. Furthermore, in additional embodiments, strands of Kanthal and some amount of metal foil or mesh, such as stainless steel, may be touching the Kanthal material to better distribute heat.

FIG. 5 displays a wick element 500 that comprises an induction energy absorbing mesh 501 which comprises a first mesh 503 and a second mesh 505 that are fashioned into a spiral or tube together to make a combined wick assembly that, together, wicks and evenly heats the material to be vaporized. As shown in the embodiment of FIG. 5, the first mesh 503 and the second mesh 505 are not of the same dimensions. In another embodiment, the first mesh 503 and the second mesh 505 may be formed according to the same dimensions. Further, in one embodiment, the first mesh may be FeCrAl alloy combined with the second mesh that comprises an inert metal mesh such as, for example, stainless steel.

FIG. 6 displays a wick element 600 made from a mesh 601 that has two or more materials woven together that provide for effective and simultaneous wicking and heating of the vaporizable substance. In one embodiment, the mesh 601 may comprise an inert mesh with a fraction of the strands in one or both directions replaced with high induction-energy absorbing material such as FeCrAl alloy.

If the user wishes to directly vaporize extracts from plant material, then the same principle of induction heating can be used by replacing a liquid soaked wick element with a metal container. In embodiments, a metal container may be configured to heated by induction but may also allow airflow through the plant material. The metal container may be a sheet of mesh with the plant material rolled up in the sheet or it may be a solid or mesh cylinder with or without fins projecting into the volume of the cylinder. The spiral of foil or mesh and/or fins, allows the wick element to have little or no volume of plant material that is too far from a heated surface.

Figure 7:
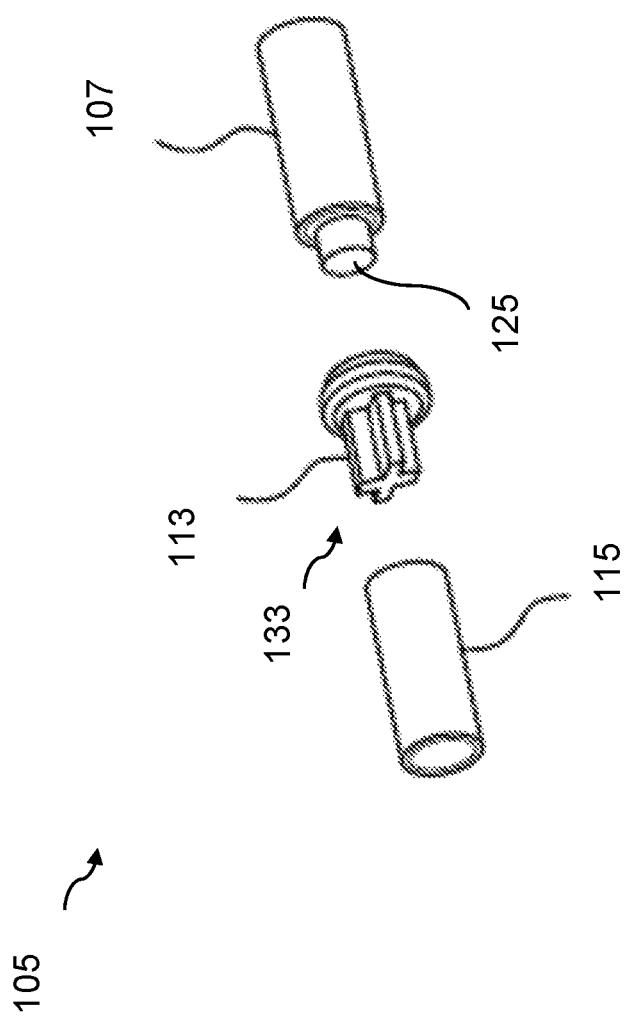
FIG. 7 is a disassembled view of components of a vaporizer device according to the present disclosure.

FIG. 7 displays a disassembled view of the tube 115, valve 113, and cartridge 107 as shown in FIG. 3. The valve 113 is configured to control airflow and seal off the reservoir when the vaporizer device 100 is not in use. The valve 113 may be sized and configured to fit over an end of the cartridge 107 that has an aperture 125. In addition, the valve 113 may have a shape that allows for precise attachment to the cartridge 107 and that is sized and configured to contact or rest on the end of the induction coil to place the cartridge 107 within the induction coil 121. The cartridge 107 may be entirely within the induction coil 121 or only a portion of the cartridge 107 may be within the induction coil 121. In embodiments, the valve 113 may be electronically controlled and may be configured to remain closed until activation of the vaporizer device 100 by a user by way of the activation button 103, for example. The valve may also be manually controlled by a thread or ramp in the mouth piece. Where the thread or ramp controls the gap between the valve and the top of the cartridge. The valve may be made of any material as appropriate, such as plastic, rubber, fiberglass, metal, and glass. In one embodiment the valve is made from a suitable grade of silicone rubber.

The tube 115 is sized and configured to be placed over an end 133 of the valve 113 that is distal from the cartridge and directs the vapor or aerosol from the vaporizable substance out of the mouthpiece component 117. In one embodiment, the tube 115 is a cylinder. The tube 115 may be formed any material that is appropriate, including, for example, glass. The tube 115 is configured to work with the valve to adjust airflow into and/or out of the vaporizer device 100 and, when closed, prevents leakage of the vaporizable substance.

Power is provided to the induction coil 121 from the power source 111. According to embodiments, the power source 111 may be any form of a device that consists of one or more electrochemical cells that convert stored chemical energy into electrical energy that is sized appropriately for the application. Accordingly, the power source 111 may be a battery, for example, which may be a primary battery or a secondary, or a rechargeable, battery. Further, the battery may be an alkaline battery, a watch battery, or Lithium Ion battery.

According to at least one embodiment, the electronic components of the vaporizer device 100 comprise a circuit that includes a current generating device, a processor, and at least one sensor. The power supplied to the induction coil can be controlled by the processor, which provides precise monitoring and control of the power supplied to the induction coil on a time scale that may be as low as a few milliseconds. According to embodiments, the processor is configured to receive information from the sensor and is able to adjust a heating profile applied to the wick element by the induction coil. The sensor may be able to detect or calculate such information as airflow from or into the vaporizer device, pressure at locations within the vaporizer device or of the vapor exiting device, and/or temperature of the components or locations near the components of the vaporizer device 100, such as the temperature of the induction coil. This would, for example, allow the circuit to sense that the user of the vaporizer device 100 is beginning to inhale and that a power level needs to increase to compensate for a tendency of the incoming air to cool the wick element below its ideal temperature. When an active inhalation is not in progress, the circuit may be able to then reduce the power to improve the life of the power source.

The processor may also be able to use this information to calculate and implement an optimal temperature profile. Furthermore, the processor may be configured to adjust a heating profile applied to the wick element by the induction coil based on the vaporizable substance. Therefore, the processor may be able to implement a predetermined heating profile according to the vaporizable substance. The processor may also allow the user to modify the settings or even the entire algorithm for providing the heat in order to obtain a best experience. The design and configuration of all of the electronic components can be sufficiently energy efficient to allow the vaporizer device to be hand held and battery operated. Additionally, the electronic components may comprise a printed circuit board and, according to embodiments, the processor may be a microprocessor or a microcontroller.

In another embodiment, the cartridge may comprise an identifier that comprises content information regarding the contents of the cartridge and the identifier may be incorporated into the cartridge such as with a barcode or other mechanism that provides a signal regarding a vaporizable substance and/or wick element within the cartridge. The processor may be coupled to the induction heating element and programmed to read the content information of the cartridge so that it is used to set parameters and cause the induction heating element to apply a heating profile to the vaporizable substance according to content information of the cartridge.

Figure 8C:
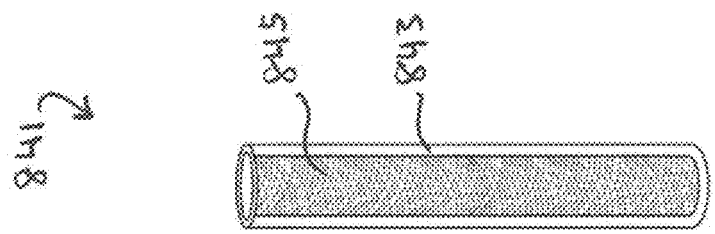
FIG. 8c is another embodiment of a cartridge of a vaporizer device according to the present disclosure.
Figure 8B:
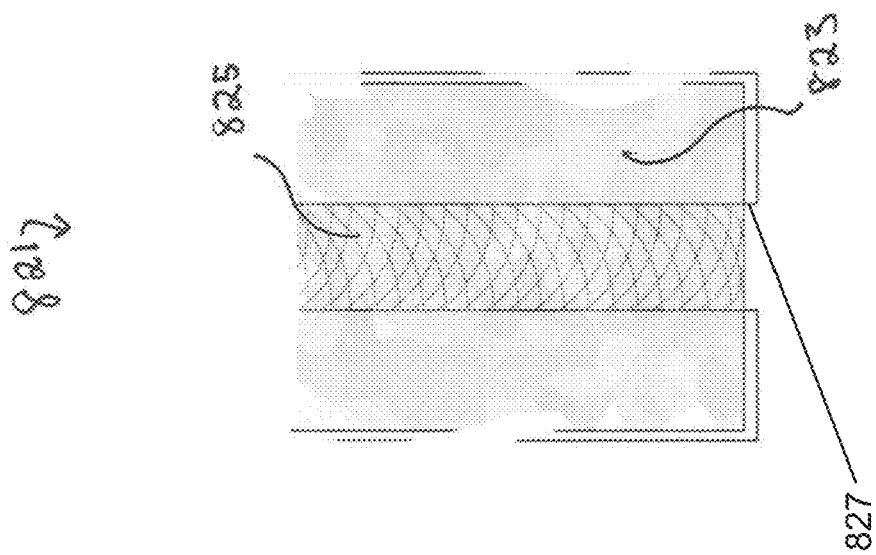
FIG. 8b is another embodiment of a cartridge of a vaporizer device according to the present disclosure.
Figure 8A:
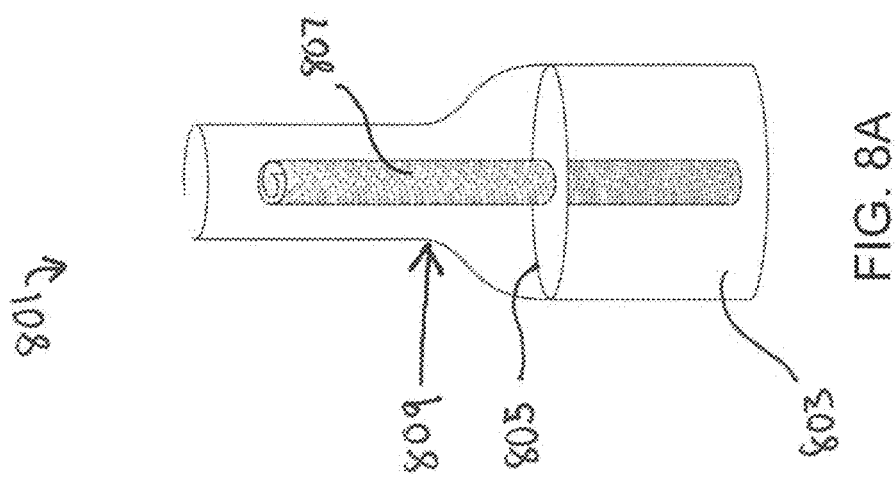
FIG. 8a is an embodiment of a cartridge of a vaporizer device according to the present disclosure.

FIGS. 8A-8C display configurations of cartridges for various vaporizable substances. Each cartridge may be configured to be easily exchanged and may be reusable or single use. Each cartridge may also comprise markings that are etched or printed on the cartridge to allow the vaporizer device to detect and adapt vaporization parameters to the contents being vaporized. According to embodiments, the vaporization parameters may comprises a heating profile to be applied to the vaporizable substance, which may include constraints on temperature of the wick element, pressure of air incoming or outgoing from the vaporizer device, and timing of the application of heat to the vaporizable substance. In other embodiments, each of the cartridges may comprise a microchip that is able to be read by a processor on the vaporizer device 100 to determine the contents of the cartridge and adapt vaporization parameters accordingly.

As shown in FIG. 8A, a cartridge 801 comprises a reservoir 803 containing an e-liquid 805 or similar material to be vaporized and a wick element 807 that acts as a combined wick and inductively heated material. According to the embodiment of FIG. 8A, the cartridge 801 may have a constriction 809 that separates the neck 811 of the cartridge 801 from the reservoir 803 to prevent leaking of the liquid 805 from the reservoir 803. As shown in FIG. 8B, a cartridge 821 contains loose leaf material 823 with volatile components to be vaporized. The cartridge 821 has an opening 827 in at least one end that allows for refilling the cartridge 821. In another embodiment, the cartridge may have an opening at each end. A wick element 825 shown in FIG. 8B is formed as a mesh; however, in other embodiments the wick element may take on other forms as discussed as appropriate. As shown in FIG. 8C, a cartridge 841 contains a wax material 843 or oil material to be vaporized and the wick element 845 comprises a mesh that is impregnated with the wax or oil material 843 to be vaporized.

As the cartridges allow for refilling and/or replacement, along with a variety of substances, a vaporizer device as described herein may be used as a general drug delivery system that could deliver drugs including medical marijuana and medicines that are vaporizable other than medical marijuana.

Referring back to FIG. 3, in another embodiment, the vaporizer device 100 may be provided with a communication connection to a computer device such as a USB port, wireless Bluetooth, or other connection that would allow for changes to settings, preferences, or algorithms involved in the operation of the vaporizer device. In embodiments where the vaporizer device comprises a physical connection such as a USB port, the physical connection would enable charging with via that connection as well.

The USB port or other computer connection may facilitate communication with the microprocessor/microcontroller to enable changes and to verify the compatibility of hardware with software. By allowing hardware and software changes to the vaporizer device, few components may be swapped or even just the microprocessor/microcontroller code changed to enable different materials to be used or to allow different inhalation experiences by the user. Software, written to analyze and communicate with the device, will allow for greater control and variability of the induction heating element. Changes made in software will adjust the electronic control components onboard, such as a processor, as well. Users may be able to vary how hot a wick element gets as well as change the wick element itself. The USB port or other computer connection may also allow remote monitoring of the status of a vaporizer device by a manufacturer or retailer to improve product reliability but also to protect intellectual property by ensuring that only original manufactured components are used in the vaporizer devices. Also, in embodiments that include a rechargeable battery as the power source, the connection, such as the USB port, may also serve as the charger connector.

According to embodiments, the power source may comprise of a current generating device which may include an oscillating circuit. The oscillating circuit is configured to excite the required electro-magnetic field in the induction coil. The oscillating current may be of an energy efficient design and would operate at a frequency between a few tens of Hz to many megahertz. In embodiments, an AC current frequency is likely to be most effective in the hundreds of kHz range but may be suitable up to frequencies of many MHz. A suitable frequency that matches the skin depth of the electromagnetic penetration with the wire thickness of the wick element will results in optimal conditions. Other materials and arrangements of the wick element may provide different optimal frequencies.

Figure 9:
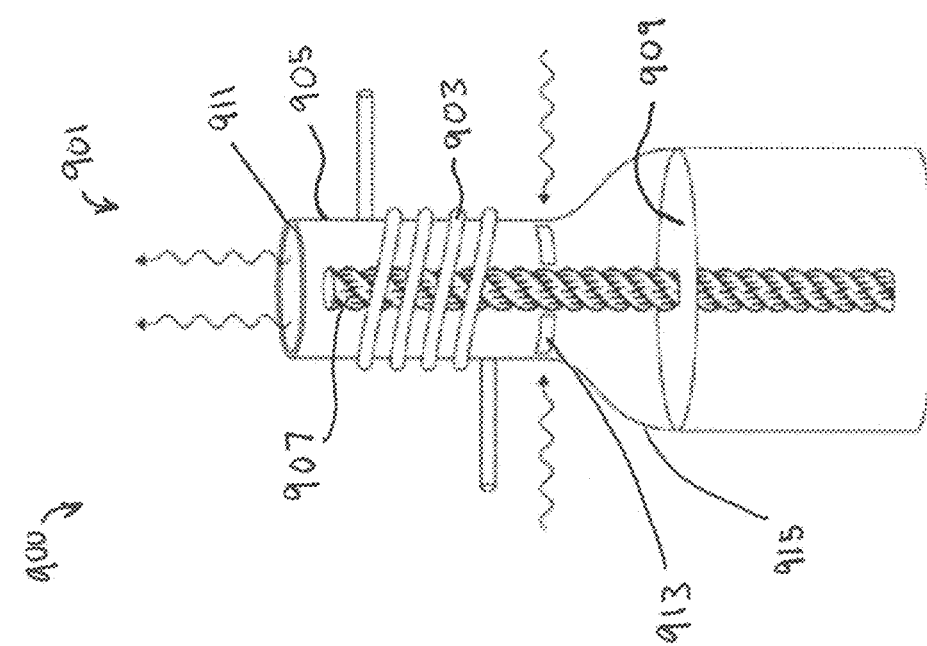
FIG. 9 is an illustration of a configuration of components of a vaporizer device according to the present disclosure.

FIG. 9 demonstrates a cartridge configuration 900 according to an embodiment of the present disclosure with an induction coil 903 adjacent a portion of a cartridge 901. The induction coil 903, shown in FIG. 9, is configured around a neck 905 of the cartridge 901 and a wick element 907 is disposed within a liquid reservoir 909 of the cartridge 901. AC electric current is applied to the induction coil 907 to create an electromagnetic induction field around the wick element 907. Additionally, the airflow to be inhaled exits through a top 911 of the cartridge 901 and subsequently the mouthpiece component 117 of the vaporizer device 100. Incoming air, which mixes with the vapor or aerosol of the vaporizable substance, are also shown in FIG. 9. The incoming air may be received into the cartridge 901 through at least one air intake, or aperture 913, in a body 915 of the cartridge 901. Additionally, apertures may be provided in the housing 109 to correspond with the at least one air intake 913. The air intake 913 shown in FIG. 9 comprises two apertures in the neck 905 of the cartridge 901; however, the number, shape, and size of the at least one air intake 913 may vary as deemed appropriate for the application. Furthermore, in embodiments, the at least one air intake 913 may configured such that the vaporizable substance is not able to leak out of the cartridge 901 in any appreciable amount when the cartridge 901 is tipped.

The wick element 907 shown in FIG. 9 is formed as a stranded wick element, however, any size and configuration of a wick element as described herein may be used as appropriate. The vaporizable substance is a liquid that is transported through the wick element 907 via a capillary or wicking action. In one embodiment, the liquid is an e-liquid, vaping liquid, an e-juice, liquid nicotine, or other form of liquid that produces an inhalable vapor or aerosol. In another embodiment, the vaporizable substance comprises a waxy material, oily material, or even a plant material, that is less viscous than conventional e-liquid. In such an embodiment, a smaller cartridge may be used such that the wick element, alone, comprises the vaporizable material and a liquid reservoir is not necessary. In various other embodiments, the cartridge comprises a wick element, such as a mesh or stranded element that is impregnated with a wax or oil. The wick element may act as a kind of sponge to hold in the wax or oil.

Figure 10:
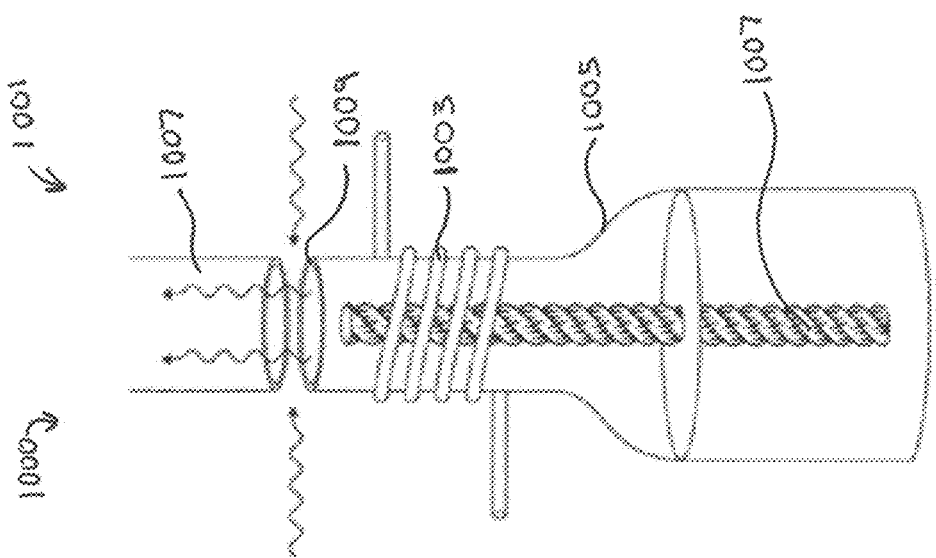
FIG. 10 is an illustration of another configuration of components of a vaporizer device according to the present disclosure.

FIG. 10 demonstrates a cartridge configuration 1000 according to another embodiment of the present disclosure with an induction coil 1003 adjacent a portion of a cartridge 1001 that is similar to that of what is shown in FIG. 9. The cartridge 1001, however, shown in FIG. 10, does not have an air intake on a body 1005 of the cartridge 1001. As shown in FIG. 10, incoming air mixes turbulently with the vapor or aerosol produced as a wick element 1007 heats the vaporizable substance, and the vapor or aerosol exits a top 1009 of the cartridge 1001. A tube 1007, similar to that of what is described above with regard to FIG. 3, is shown. Accordingly, the tube 1007, which is separate from the cartridge 1001, defines an air path through the vaporizer device 100.

Figure 11:
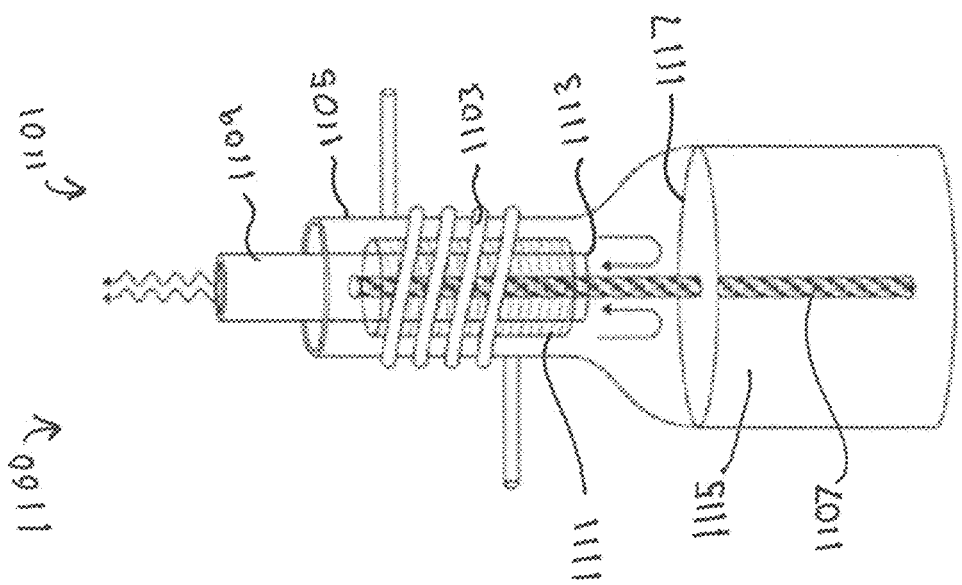
FIG. 11 is an illustration of another configuration of components of a vaporizer device according to the present disclosure.

FIG. 11 demonstrates a cartridge configuration 1100 according to an embodiment of the present disclosure with an induction coil 1103 around a neck 1105 of a cartridge 1101, a wick element 1107, an insulating member 1109, and a preheating element 1111. The wick element 1107 enters a first open end 1113 of the insulating member 1109 and is located within a chamber of the insulating member 1109, such as an insulating tube. The preheating element 1111 is located around an outside surface of the insulating member 1109. In the embodiment shown in FIG. 11, the preheating element 1111 is concentric with the wick element 1107 and surrounds a portion of the insulating member 1109 in which the wick element 1107 is located. In another embodiment, the preheating element 1111 and the wick element 1107 may not overlap with respect to a portion of the insulating member 1109. The wick element 1107 is configured and functions similar to the wick element shown in FIGS. 9 and 10, such that it is contacts a liquid 1117 in a reservoir 1115 of the cartridge 1101. The liquid 1117 is able to move up, or though, the wick element 1107 according to a capillary action. The induction coil 1103 is charged with an AC current to generate a magnetic filed that creates electric current in the preheating element and the wick element.

Preheating the wick element may provide a more responsive vaporizer device 100. Employing the preheating element 1111 narrows the temperature range that the vaporizable substance or material is exposed to. When there is a strong airflow that is not preheated, it cools the wick down. In such a situation, power to the wick element may need to be higher than is optimal to pre-compensate for the cooling effect. With a preheater, the air is heated before it gets to the wick element and so the wick can be at a lower temp and still make a good aerosol.

Additionally, the airflow to be inhaled and the incoming airflow into the cartridge 1101 are shown. The insulating member 1109 provides a path for the airflow to be inhaled and is configured to allow incoming air to pass between the insulating member 1109 and the neck 1105 of the cartridge 1101. The preheating element 1111 may act as an upstream heating element, for example. Accordingly, if the airflow is arranged so that there are two concentric tubes with the incoming air flowing down, the single induction coil 1103 surrounds both the preheating element 1111 and the wick element 1107 heating them with the same oscillating electromagnetic field. The relative temperatures and heating effectiveness of the two passive heating elements, the preheating element 1111 and the wick element 1107, may then be adjusted by their relative size and material properties to give the best experience to the user. In one embodiment, the induction coil 1107 may generate a current in the preheating element 1111 prior to creating a current in the wick element 1107. In addition, current may be generated in the preheating element 1111 and the wick element 1107 contemporaneously.

Figure 12:
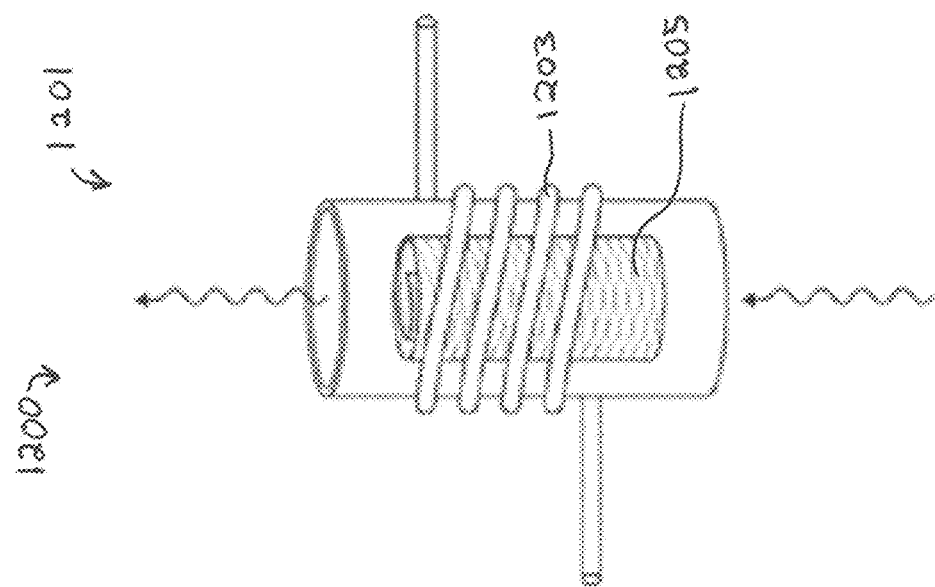
FIG. 12 is an illustration of another configuration of components of a vaporizer device according to the present disclosure.

FIG. 12 demonstrates a cartridge configuration 1200 according to an embodiment of the present disclosure with an induction coil 1203 around a cartridge 1201 and a wick element 1205. As shown in FIG. 12, the wick element 1205 is a rolled up mesh. The airflow to be inhaled and the incoming airflow flow linearly through the cartridge 1201. The mesh may be impregnated with the vaporizable substance that is in the form of a solid or semi solid that will not flow away from the wick element 1205. In one embodiment, the mesh may be impregnated or surrounded by a plant material. In addition, a binder material that melts at a higher temperature than the vaporizable substance may be added to keep the vaporizable substance in an adjacent relationship to the wick element 1205.

Figure 13:
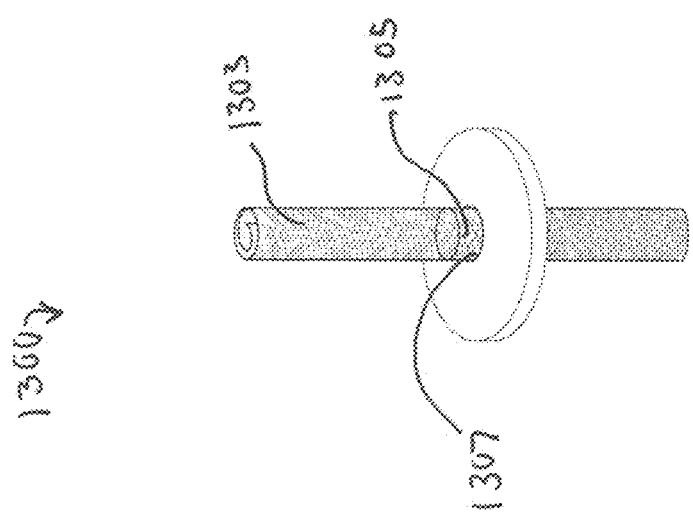
FIG. 13 is an illustration of another configuration of components of a vaporizer device according to the present disclosure.

FIG. 13 demonstrates a cartridge configuration 1300 according to an embodiment of the present disclosure with a cartridge having a neck, an insulating member, and wick element 1303 having a sealing portion 1305 that moves from an open position to a closed position. Since the cartridge and wick element 1303 can be separated from any electrical connections, this provides an opportunity to improve leak proofing of a reservoir of the cartridge. While an induction coil would be present, it is not shown for clarity of the other components. The sealing portion 1305 acts similar to that of a cork. The sealing portion 1305 is configured to close an opening 1307 of the cartridge and seal a reservoir of the cartridge when the sealing portion 1305 is in the closed position when vaporizer device is not in use. A user may be able to move the sealing portion 1305 to an open position based on a small motion of a component of the vaporizer device, such as a button. The small motion would move the sealing portion 1305 to the open position and allow the liquid in the reservoir to move freely in the wick element 1303.

Figure 14:
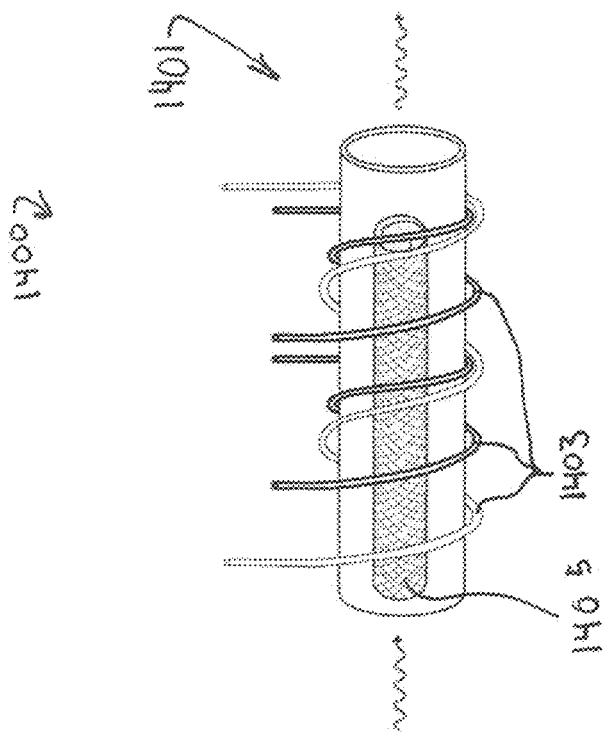
FIG. 14 is an illustration of another configuration of components of a vaporizer device according to the present disclosure.

FIG. 14 demonstrates a cartridge configuration 1400 according to an embodiment of the present disclosure with multiple, additional heating elements 1403 around a cartridge 1401 and a wick element 1405 located within the cartridge 1401. The multiple heating elements 1403 are shown as multiple induction coils along the length of the cartridge 1401. In other embodiments, the additional heating elements 1403 may be resistive heating elements or induction heating elements. As shown in FIG. 14, the wick element 1405 is a rolled up mesh. Each induction coil may be activated separately so that heat is generated in sections of the wick element and not necessarily continuously or in a linear fashion. Heating the wick element 1405 in this fashion may prolong the life of the vapor, and/or wick element, for example. Furthermore, according to embodiments, the additional heating elements 1403 may be of different sizes and/or inductances, may have different power requirements, and may or may not overlap. According to embodiments, this is configuration may be applied to a cartridge that uses loose leaf material but also applies to the cartridges that vaporize waxy and e-liquid materials.

The induction coils may be excited in versatile ways to achieve different effects. The induction coils can be excited to produce a constant heat gradient profile or to move a hot zone along the length of the wick element in time or to provide a time dependent heat profile. The coils may also be excited at different frequencies to more effectively heat different components in the wick element. In one embodiment, the induction coils are activated according to a predetermined order. The order may be defined according to the most effective way to heat the wick element or the order may be defined according to the vaporizable substance associated with the wick element. In one embodiment, the wick element may be impregnated with different vaporizable substances along the length of the wick. Accordingly, the induction coils can be activated to produce a mixture of the vapors or aerosols produced by the different substances in flavors that are pleasing to a user. In one embodiment, the different vaporizable substances may be different flavors designed to mimic fruits or flavors of ice cream. A mixture of such flavors may enhance the user experience with the vaporizer device. Additionally, in embodiments, the induction coils may be formed as part of a replaceable cartridge such that the cartridge structure (the cartridge body, the wick element, and the induction coils) is designed to be replaced. Such a cartridge comprises electrical connections for the induction coils to connect with the electronic control components of the vaporizable device.

A further improvement on the vaporization of extracts directly from plant material that more closely reproduces the smoking of a cigarette is to heat only a fraction of a volume at a time starting at the bottom of the charge of plant material and progressively moving the heated disk of material along the charge until all of the desired extracts have been vaporized from the plant material. This may be achieved by having, in effect, multiple induction coils along the length of the cartridge so that the induction coils can be energized in turn thus moving the hot zone along the cartridge, similar to that shown in FIG. 14. The plant material or liquid content of the different zones may also contain different flavor or varieties of plant giving a novel experience of a progression of extracts being delivered over time. The different zones may be heated to different temperatures over time and this multi-zone arrangement does not have to be collinear. The zones could be in any arrangement as long as they all deliver the vapor to the user. If the zones are arranged, not collinearly, but in parallel, it would afford the opportunity to blend the different flavors or plant materials together by choosing different excitations of the induction coils. This would allow two vapors to be delivered and blended together such as a flavored nicotine-containing e-liquid vapor being delivered together with an herbal plant extract, each of which requires a different vaporizing temperature. Accordingly, this would allow blends of combinations ranging from all e-liquid vapor to all plant extract vapor.

Figure 15:
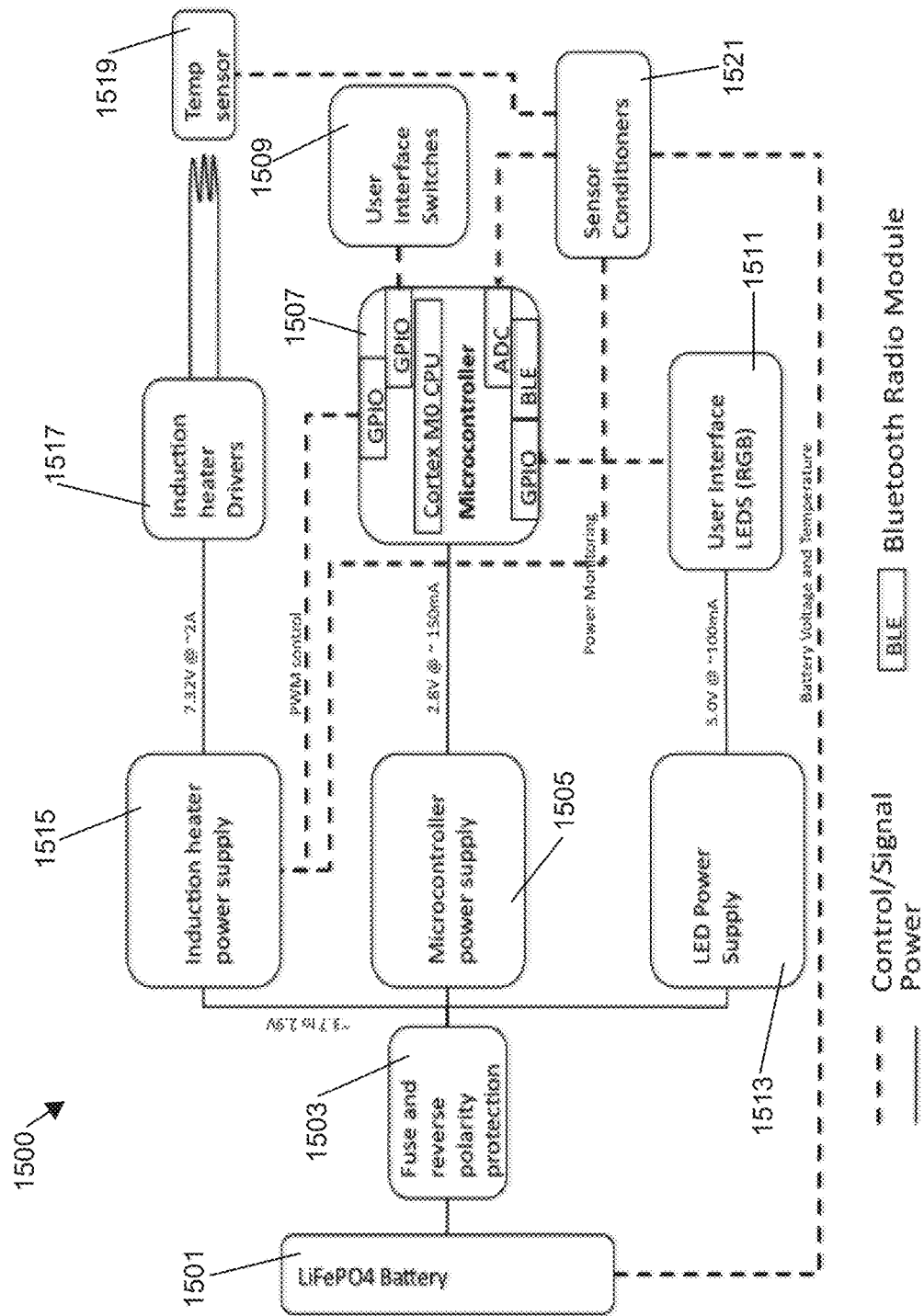
FIG. 15 is diagram of electronic components of an embodiment of a vaporizer device according to the present disclosure.

FIG. 15 illustrates a logic diagram of the aspects of the electronic components of a vaporizer device according to an embodiment of the present disclosure. The electronic control components 101 described above with regard to FIG. 3, may comprise a circuit 1500 with the functional blocks as shown in FIG. 15. In the embodiment of FIG. 15, the circuit 1500 derives its power from a battery that is used to supply three different voltage levels according to different circuit functions. The battery may be any type of battery that provides the appropriate power levels and is of an appropriate form factor. The battery may be a primary battery or a rechargeable battery.

The maximum power is consumed in circuit 1500 is by a voltage oscillator for the induction coil which is part of the induction heater drivers circuit 1517 which is fed by the induction heater power supply 1515. The induction heater drivers circuit 1517 may use around 7.3V with a power consumption of around 15 W. In the embodiment of FIG. 15, the microcontroller circuit 1507 fed by the microcontroller power supply 1505 uses and the LED supply circuit 1511 is fed by the LED power supply 1513 require less power. In other embodiments, the voltages levels may be different according to the voltage, amperage, and power requirements of different components. The induction heater power supply 1515, the microcontroller power supply 1505, and the LED power supply 1513 are all fed by a Lithium iron phosphate (LiFePO4) rechargeable battery 1501 through a fuse and reverse polarity protection circuit 1503, which protects components of circuit 1500.

The microcontroller 1507 comprises a plurality of General Purpose Input/Outputs (GPIO) that couple the microcontroller 1507 to the induction heater power supply 1515, the user interface LEDs 1511, and the user interface switches 1509. The microcontroller 1507 provides Pulse Width Modulation (PWM) control signals to the induction heater power supply 1515. The microcontroller 1507 also includes a Bluetooth component (BLE) that allows the microcontroller 1507 to communicate with other components as appropriate. The microcontroller shown in FIG. 15 is an ARM Cortex M0 processor designed by ARM Holdings. According to embodiments, other processors, controllers, circuit components, etc. may be used as appropriate. In additional embodiments, the functions of the microcontroller/microprocessor of the vaporizer device may be implemented with analog circuitry as appropriate. The sensor conditioners 1521 sense the power parameters, battery voltage and temperature of the battery, provided by the battery 1501 and provide signals to components of circuit 1500 as appropriate. The sensor conditioners 1521 then provide a signal to the microcontroller 1507 which is input to an AC/DC (ADC) converter of the microcontroller 1507. The sensor conditioners 1521 also provide signals to the induction heater power supply 1515 and temperature sensor 1519.

Temperature sensor 1519 senses the temperature at or near the wick element that is heated by the magnetic field from the induction coil. Temperature sensor 1519 is able to verify that the induction coil is heating the wick element properly based on communication with the induction heater drivers 1517. The user interface switches 1509 and user interface LEDs 1511 (Red Green and Blue) allow a user to interact with a vaporizer device and to receive feedback from the device.

Embodiments of the microcontroller/microprocessor of the vaporizer device automatically run a piece of software called the firmware. This software responds to user inputs and controls the power to the induction heater oscillator, senses the temperature, voltage and current to the induction heater coil and state of the battery and communicates via Bluetooth to a host device. According to user inputs and data sensed, the firmware also turns the feedback LED's on with a specific color to indicate a desired property examples of which are the state of battery charge (green could be >50%, yellow 15%-49%, red <15% and flashing red <5%) or simply that the device is on, in pre-heat mode or draw cycle.

In a simple embodiment of the firmware/device combination, the device functions as follows in a typical user setting. Pressing the button cycles through the following sequence:

1—press/release to power the device on
1—press/release to put the device from Power On to Pre-Heat mode
1—press to put the device from Pre/Idle Heat to Draw Heat mode
1—release to put the device from Draw Heat into Idle Heat mode
3—quick press/releases from any mode to power the device off.

On startup, the firmware checks the status of the battery and all inputs and then waits for input from the user via the button. Once the button is depressed, the firmware performs the following functions depending on the current and previous state of the instrument:

In initial power on mode, the device can be accessed using a smart phone or other suitable Bluetooth device, any settings can be interrogated as well as data like the number of puffs etc. can be downloaded, One press from startup goes to pre-heat mode. In this mode, the device maintains the vaping material at a predetermined temperature so that there is less delay when the device is changed to the next setting. A second press initiates the draw cycle. The firmware increases the power to the coil to a predetermined level that gives a desirable and safe vapor for all the time the button is depressed. On button release, the device returns to pre-heat mode. This is repeated for the duration that he user wishes to use the device. A sequence of 3 button presses may be used to turn the device off.

Firmware code for embodiments of the vaporizer device to perform the functions disclosed herein is reproduced here:

```
int main(void)
{
    // Initialize
    timers_init(); //initialize timers
    gpiote_init(); //initialize general purpose input-output
//
// !!! - 06APR2015, GWA - ADDED TO SUPPORT SEGGER RTT LOGGING
    // For errors use: loge("!!! ASSSERT ERROR: %d", s_error_code)
    // For warnings use: logw(""Warning: Something")
    // For information use: logi("Info: (%d)", infoValue)

SEGGER_RTT_ConfigUpBuffer(0, NULL, NULL, 0, SEGGER_RTT_MODE_BLOCK_IF_FIFO_FULL);
    SEGGER_RTT_WriteString(0, "SEGGER Real-Time-Terminal Start\r\n\r\n");
    SEGGER_RTT_WriteString(0, "###### Testing SEGGER_printf() ######\r\n");
    buttons_init(); //initialize button handler
    ble_stack_init(); //initialize bluetooth
```

```
    scheduler_init(); //initialise scheduler
    gap_params_init(); // initialise gap parameters
// !!! - 01APR2015, GWA - ADD NVM INIT, CHECK AND UPDATE NVM STORED VARIABLES
    NvmParmasInit(); //initialize non volatile memory
    services_init(); //initialize services
    advertising_init(); //initialize bluetooth advertising
    conn_params_init(); //initailize connection parameters
    sec_params_init();
    leds_init(); //initialize light emitting diods
    // Init device
    EvokeInit(); //initialize the evoke device
    // Start execution
    timers_start();
    advertising_start(); //bluetooth
    // Configure and enable the watchdog timer
    wdt_init();

// Enter main loop
    for (;;)
    {
        // Run scheduler and execute queued events
        app_sched_execute();

// Manage power
        power_manage();

// Clear the watchdog timer
        NRF_WDT->RR[0] = WDT_RR_RR_Reload;   //Reload watchdog register 0
    }
}
```

COMMENTED MAIN

```
/***************************************************************************/
/* File        : main.c                              */
/* Date        : 18Dec2014                           */
/* Description : main body progream for Loto "Evoke" device.        */
/*                                                   */
/* Updates (UNDER DEVELOPMENT):                      */
/*        18Dec2014, GWA - Initial version. Just basic function    */
/*                  shell based on blinky example.         */
/*        29Dec2014, GWA - Added files to support S110 BTLE        */
/*                  peripheral softdevice. Re-structured   */
/*                  project and main.c around ble_app_hrs  */
/*                  example project for testing.           */
/*                  Add files from n5 SDK to use with      */
/*                  Dynastream battery i/o board.          */
```

```
/*      08Jan2015, GWA - Replaced body of main.c to pattern device    */
/*                      on ble_app_prox project.                      */
/*      15Jan2015, GWA - Modified main.c around custom service        */
/*                      profile for Evoke BT characteristics.         */
/*      16Jan2015, GWA - Add battery service and ADC conversion.      */
/*      02Feb2015, GWA - Move battery post ADC processing from ISR    */
/*                      to application. Add sensor read function.     */
/***************************************************************/
/***************************************************************/
/*                      INCLUDES                        */
/* #include omitted to reduce line count - this is lest of include files
/***************************************************************/
/*, <stdint.h>, <string.h>, <math.h>, "nordic_common.h", "nrf.h", "app_error.h",
/*"nrf_gpio.h", "nrf_delay.h", "nrf51_bitfields.h", "ble.h", "ble_hci.h",
/*"ble_srv_common.h", "ble_advdata.h", "ble_conn_params.h", "boards.h",
/*"app_scheduler.h", "softdevice_handler.h", "app_timer.h", "ble_error_log.h",
/*"app_gpiote.h", "app_button.h", "ble_debug_assert_handler.h", "pstorage.h",
/*"ble_evs.h"
/*// !!! - 16JAN2015, GWA - ADDED TO SUPPORT BATTERY MONITOR SERVICE,
/*"ble_bas.h", "app_pwm.h", "app_led.h"
/*// !!! - 09FEB2015, GWA - ADDED FOR BSP LED SUPPORT, "evoke_bsp.h", "evoke.h"
/*// !!! - 27MAR2015, GWA - ADDED FOR NVM STORAGE AND RETRIEVAL, "pstorage.h"
/*// !!! - 02APR2015, GWA - ADDED DEVICE INFORMATION SERVICE, "ble_dis.h"
/*// !!! - 06APR2015, GWA - ADDED TO SUPPORT SEGGER RTT LOGGING, <stdio.h>,
/*"SEGGER_RTT.h", "rtt_log.h"
/***************************************************************/
/*                      VARIABLES                       */
/***************************************************************/
// State-type of current ADC conversion
static adc_conv_t         m_adc = ADC_READY;
// Holds sensor ADC data
static uint8_t            m_adcBat = 50;    // Battery ADC
static uint8_t            m_adcTemp1;       // Temperature sensor ADC
static uint8_t            m_adcVosc;        // Oscillator voltage ADC
static uint8_t            m_adcIosc;        // Oscillator current ADC
// Iosc samples
static uint8_t   m_OscCurrent = 0;
// !!! - 31MAR2015, GWA - REPLACE INDIVIDUAL VARIABLES (BELOW) WITH A SINGLE TYPE DEFINITION
static heatProfile_t heatProfile;
//static uint8_t htrIdleDutyCycle = DEFAULT_HEAT_IDLE_DC;       // Idle (post-draw) duty cycle in mS
//static uint8_t htrDrawDutyCycle = DEFAULT_HEAT_DRAW_DC;       // Duty cycle when draw button is initially pressed
//static uint8_t htrExtDrawDutyCycle = DEFAULT_HEAT_EX_DRAW_DC; // Duty cycle when draw button is held after draw timeout expires
//static uint8_t htrPreheatDutyCycle = DEFAULT_HEAT_PREHEAT_DC; // Duty cycle when heater is initially activated
//static uint16_t htrDrawTimeOut = DEFAULT_HEAT_DRAW_TO;        // Timeout to revert to extended-draw duty cycle when draw button is held
// Evoke device state
```

```
static evoke_t              m_evoke;  // Operational state of the device
// !!! - 19JAN2015, GWA - ADDED SENSOR READ TIMER
static app_timer_id_t       m_sensor_timer_id;         // Sensor measurement timer
static app_timer_id_t       m_draw_heat_timer_id;      // Time out for draw heat level
static ble_gap_sec_params_t m_sec_params;              /**< Security requirements for this application. */
static uint16_t             m_conn_handle = BLE_CONN_HANDLE_INVALID;   /**< Handle of the current connection. */
static ble_evs_t            m_evs;
// !!! - 16JAN2015, GWA - ADDED TO SUPPORT ADC FOR BATTERY MONITOR SERVICE
static ble_bas_t            m_bas;                     /**< Structure used to identify the battery service. */
static app_timer_id_t       m_battery_timer_id;        /**< Battery measurement timer. */
static void on_bas_evt(ble_bas_t * p_bas, ble_bas_evt_t * p_evt);
// !!!- END ADDED CODE
static uint16_t schData;   // For passing NO data to the Nordic application scheduler...
static bool adc_enabled = false;   // flsg indicating ADC is ready for use
// Heat oscillator startup timer
static app_timer_id_t       m_osc_start_timer_id;
// !!! - 13APR2015, GWA - ADDED FOR POWER SUPPLY THERMAL OVERLOAD SHUTDOWN DETECTION
// Power supply thermal overload detection count
static app_timer_id_t       m_pwrTOL_timer_id;
static uint16_t             m_pwrTOL_oscCount;
// !!! - 16MAR2015, GWA - ALTERNATIVE BUTTON HANDLER DEV CODE
static app_timer_id_t       m_button_timer_id;
// !!! - END DEV CODE
// !!! - 05MAY2015, GWA - ADDED/REVISED TO SUPPORT ONE-BUTTON OPERATION
static app_timer_id_t       m_state_timer_id;
static app_timer_id_t       m_activity_timer_id;
// !!! - 27MAR2015, GWA - ADDED FOR NVM STORAGE AND RETRIEVAL
static uint8_t pstorage_wait_flag = 0;
static pstorage_block_t pstorage_wait_handle = 0;
// Handle for all storage allocated in NVM for this application
static  pstorage_handle_t   paramStorageHandle;
// Handles for heat profile NVM storage
static      pstorage_handle_t       profile_0_handle;
//static    pstorage_handle_t       profile_1_handle;
//static    pstorage_handle_t       profile_2_handle;
// !!! - 17APR2015, GWA - TEST CODE, LED PWM CONTROL UPDATE TIMER
//static app_timer_id_t  m_led_timer_id;
// !!! - 05MAY2015, GWA - ADDED TO SUPPORT ONE-BUTTON OPERATION
static uint32_t  m_runTime;
static buttonStatus_t m_ButtonStatus;
/*****************************************************************/
/*                      PROTOTYPES                               */
/*****************************************************************/
// Persistent storage system event handler
//void pstorage_sys_event_handler (uint32_t p_evt);
static void EvokeSetState (device_state_t state);
```

```
static void EvokeStateHandler (void * p_context);
static void adc_start(adc_conv_t adcRead);
void LED_On(uint32_t led);
void LED_Off(uint32_t led);
//static void ReadSensors ( void *data, uint16_t size );
static void ReadTemp1 ( void *data, uint16_t size );
static void ReadVosc ( void *data, uint16_t size );
static void ReadIosc ( void *data, uint16_t size );
static void ReadBattV (void *data, uint16_t size);
// !!! - 13APR2015, GWA - CALCULATES PERCENT BATTERY CHARGE
static uint8_t PercentBatteryCharge(const uint16_t mvolts);
void HeaterOn ( void );
void HeaterOff ( void );
static void draw_heat_timeout_handler(void * p_context);
void HeatSet ( heat_level_t setting );
void CheckOscStart( void );
static void osc_start_timeout_handler(void * p_context);
// !!! - 13APR2015, GWA - ADDED FOR POWER SUPPLY THERMAL OVERLOAD PROTECTION
void CheckTOLStart( void );
void PwrSupplyTOL_Detect( void );
void LPCOMP_Init ( void );
void LPCOMP_Disable ( void );
void EvokeSleep( void );
// !!! - 16MAR2015, GWA - ALTERNATIVE BUTTON HANDLER UNDER DEVELOPMENT
void Alt_ButtonInit ( void );
static void Alt_ButtonTOHandler(void * p_context);
uint8_t Alt_ButtonGetStates ( void );
void Alt_ButtonHandler ( void );
void SetDeviceInd (device_ind_t indication);
int16_t conv_temp (uint8_t adcValue);
// !!! - 27MAR2015, GWA - ADDED FOR NVM STORAGE AND RETRIEVAL
// Persistent storage system event handler
//void pstorage_sys_event_handler (uint32_t p_evt);
//static void pstorage_test_store_and_update(void);
static void NvmParmasInit(void);
static void StoreHeatProfile ( void );
static void GetHeatProfile ( void );
static void nvm_param_cb_handler(pstorage_handle_t * handle,
                                                                    uint8_t op_code,
                        uint32_t    result,
                        uint8_t     * p_data,
                        uint32_t    data_len);
static void gpiote_init(void);
static void RunTimerInit(void);
void RunTimerStart (void);
void RunTimerStop (void);
```

```
void RUN_TIMER_IRQHandler(void);
uint32_t RunTimeGet (void);
void ActivityTOHandler( void * p_context );
/*******************************************************************/
/*                    FUNCTIONS                        */
/*******************************************************************/
/**@brief Function for error handling, which is called when an error has occurred.
 *
 * @warning This handler is an example only and does not fit a final product. You need to analyze
 *          how your product is supposed to react in case of error.
 *
 * @param[in] error_code  Error code supplied to the handler.
 * @param[in] line_num    Line number where the handler is called.
 * @param[in] p_file_name Pointer to the file name.
 */
void app_error_handler(uint32_t error_code, uint32_t line_num, const uint8_t * p_file_name)
{}
/**@brief Callback function for asserts in the SoftDevice.
 *
 * @details This function will be called in case of an assert in the SoftDevice.
 *
 * @warning This handler is an example only and does not fit a final product. You need to analyze
 *          how your product is supposed to react in case of Assert.
 * @warning On assert from the SoftDevice, the system can only recover on reset.
 *
 * @param[in]  line_num   Line number of the failing ASSERT call.
 * @param[in]  file_name  File name of the failing ASSERT call.
 */
void assert_nrf_callback(uint16_t line_num, const uint8_t * p_file_name)
{}
// !!! - 16JAN2015, GWA - FUNCTION ADDED TO SUPPORT ADC FOR BATTERY MONITOR SERVICE
/*******************************************************************/
/* Function:    battery_level_meas_timeout_handler            */
/* Description: Called each time the battery level measurement timer expires. */
/*              Starts the battery level ADC conversion.       */
/* Parameters:  p_context - Pointer used for passing some arbitrary  */
/*              information (context) from the app_start_timer() */
/*              call to the timeout handler.                   */
/* Return:      None                                           */
/*******************************************************************/
static void battery_level_meas_timeout_handler(void * p_context)
{}
// !!! - 02FEB2015, GWA - FUNCTION ADDED TO SUPPORT ADC FOR BATTERY MONITOR SERVICE
/*******************************************************************/
/* Function:    ReadBattV                                      */
/* Description: Designed to be invoked by the Nordic app scheduler. This  */
/*              function initiates an ADC battery voltage reading, processes */
```

```
/*        the result, and then initites a battery level update    */
/*        transmission to a BT client.                            */
/*        Note: The Nordic scheduler needs the data pointer and size */
/*           parameters to fit it's format.  But they aren't used */
/*           or needed here.                                      */
/* Parameters: data - Pointer used for passing data (NOT USED)    */
/*             size - Size of data at pointer address (NOT USED)  */
/* Return:     None                                               */
/******************************************************************/
static void ReadBattV (void *data, uint16_t size)
{}
/** @brief Function for converting the input voltage (in milli volts) into percentage of 3.0 Volts.
 *
 * @details The calculation is based on a linearized version of the battery's discharge
 *          curve. 3.0V returns 100% battery level. The limit for power failure is 2.1V and
 *          is considered to be the lower boundary.
 *
 *          The discharge curve for CR2032 is non-linear. In this model it is split into
 *          4 linear sections:
 *          - Section 1: 3.0V - 2.9V = 100% - 42% (58% drop on 100 mV)
 *          - Section 2: 2.9V - 2.74V = 42% - 18% (24% drop on 160 mV)
 *          - Section 3: 2.74V - 2.44V = 18% - 6% (12% drop on 300 mV)
 *          - Section 4: 2.44V - 2.1V = 6% - 0% (6% drop on 340 mV)
 *
 *          These numbers are by no means accurate. Temperature and
 *          load in the actual application is not accounted for!
 *
 * @param[in] mvolts The voltage in mV
 *
 * @return    Battery level in percent.
 */
// !!! - 13APR2015, GWA - CALCULATES PERCENT BATTERY CHARGE
/******************************************************************/
/* Function:    PercentBatteryCharge                              */
/* Description: Used to calculate an aproximate battery percent charge. */
/*              By no means accurate, just close.                 */
/* Parameters:  mvolts - Battery voltage in millivolts            */
/* Return:      percent charge: 0-100                             */
/******************************************************************/
static uint8_t PercentBatteryCharge(const uint16_t mvolts)
{}
// !!! - 19JAN2015, GWA - FUNCTION ADDED TO DRIVE SENSOR MEASUREMENT
/******************************************************************/
/* Function:    sensor_meas_timeout_handler                       */
/* Description: Called each time the sensor measurement timer expires. */
/*              Starts sensor read ADC conversion sequence.       */
/* Parameters:  p_context - Pointer used for passing some arbitrary */
```

```c
/*              information (context) from the app_start_timer() */
/*              call to the timeout handler.                     */
/* Return:      None                                             */
/****************************************************************/
static void sensor_meas_timeout_handler(void * p_context)
{}
/****************************************************************/
/* Function:    ReadTemp1                                        */
/* Description: Reads temperature sensor #1 and transmits result to BT client.*/
/*              Note: The Nordic scheduler needs the data pointer and size */
/*                    parameters to fit it's format, but they aren't used  */
/*                    for anything here.                                   */
/* Parameters:  data - Pointer used for passing data, NOT USED   */
/*              size - Size of data at pointer address           */
/* Return:      None                                             */
/****************************************************************/
void ReadTemp1 ( void *data, uint16_t size )
{}// !!! - 15MAR2015, GWA - OBSOLETE, REPLACED BY LPCOMP BASED VOSC READING
/****************************************************************/
/* Function:    ReadVosc                                         */
/* Description: Reads oscillator voltage and transmits result to BT client. */
/*              Note: The Nordic scheduler needs the data pointer and size */
/*                    parameters to fit it's format, but they aren't used  */
/*                    for anything here.                                   */
/* Parameters:  data - Pointer used for passing data, NOT USED   */
/*              size - Size of data at pointer address           */
/* Return:      None                                             */
/****************************************************************/
void ReadVosc ( void *data, uint16_t size )
{}
/****************************************************************/
/* Function:    ReadIosc                                         */
/* Description: Reads oscillator current and transmits result to BT client. */
/*              Note: The Nordic scheduler needs the data pointer and size */
/*                    parameters to fit it's format, but they aren't used  */
/*                    for anything here.                                   */
/* Parameters:  data - Pointer used for passing data, NOT USED   */
/*              size - Size of data at pointer address           */
/* Return:      None                                             */
/****************************************************************/
void ReadIosc ( void *data, uint16_t size )
{}
/****************************************************************/
/* Function:    ADC_Enable                                       */
/* Description: Enables ADC peripheral operation.                */
/* Parameters:  None                                             */
/* Return:      None                                             */
```

```c
/********************************************************************/
void ADC_Enable( void )
{}
/********************************************************************/
/* Function:    ADC_Disable                                    */
/* Description: Disables ADC peripheral operation.             */
/* Parameters:  None                                           */
/* Return:      None                                           */
/********************************************************************/
void ADC_Disable ( void )
{}
// !!! - 20JAN2015, GWA - MODIFY FUNCTION TO PROCESS MULTIPLE ADC SOURCES
// !!! - 16JAN2015, GWA - FUNCTION ADDED TO SUPPORT ADC FOR BATTERY MONITOR SERVICE
/********************************************************************/
/* Function:    ADC_IRQHandler                                 */
/* Description: Fetches the conversion result from the ADC, converts */
/*              the value into a percentage, and send it to a peer device. */
/* Parameters:  None                                           */
/* Return:      None                                           */
/********************************************************************/
void ADC_IRQHandler(void)
{}
// !!! - 16JAN2015, GWA - FUNCTION ADDED TO SUPPORT ADC FOR BATTERY MONITOR SERVICE
/********************************************************************/
/* Function:    adc_start                                      */
/* Description: Starts and ADC conversion for target input.    */
/* Parameters:  adcRead - ADC input to sample:                 */
/*                ADC_BATT - Battery voltage                   */
/*                ADC_TEMP_1 - Temperature sensor #1 voltage   */
/*                ADC_TEMP_2 - Temperature sensor #2 voltage   */
/*                ADC_OSC_V - Heater oscillator voltage        */
/*                ADC_OSC_I - Heater oscillator current        */
/* Return:      None                                           */
/********************************************************************/
static void adc_start(adc_conv_t adcRead)
{}
/**@brief Function for the Timer initialization.
 *
 * @details Initializes the timer module.
 */
static void timers_init(void)
{}
// !!! - 16JAN2015, GWA - FUNCTION ADDED TO SUPPORT BATTERY MONITOR SERVICE
/********************************************************************/
/* Function:    bas_init                                       */
/* Description: Initializes the Battery Service.               */
/* Parameters:  None                                           */
```

```
/* Return:    None                                    */
/**************************************************************/
static void bas_init(void)
{}
/**@brief Function for the GAP initialization.
 *
 * @details This function sets up all the necessary GAP (Generic Access Profile) parameters of the
 *          device including the device name, appearance, and the preferred connection parameters.
 */
static void gap_params_init(void)
{}
// !!! - 02APR2015, GWA - ADDED TO FACILITATE DEVICE INFORMATION SERVICE
static void dis_init(void)
{}
/**@brief Function for initializing the Advertising functionality.
 *
 * @details Encodes the required advertising data and passes it to the stack.
 *          Also builds a structure to be passed to the stack when starting advertising.
 */
static void advertising_init(void)
{}// !!! - 02MAR2015, GWA - OBSOLETE WITH ADDED DUTY CYCLE CONTROL VALUES
static void inA_write_handler(ble_evs_t * p_evs, uint16_t dutyCycle)
{}
// !!! - 01APR2015, GWA - MODIFIED TO USE HEAT PROFILE INSTEAD OF INDIVIDUAL DEFINITIONS
static void htr_draw_dc_in_wr_handler(ble_evs_t * p_evs, uint16_t value)
{}
static void htr_idle_dc_in_wr_handler(ble_evs_t * p_evs, uint16_t value)
{}
static void htr_preheat_dc_in_wr_handler(ble_evs_t * p_evs, uint16_t value)
{}
static void htr_extdraw_dc_in_wr_handler(ble_evs_t * p_evs, uint16_t value)
{}
static void htr_draw_to_in_wr_handler(ble_evs_t * p_evs, uint16_t value)
{}
/**@brief Function for initializing services that will be used by the application.
 */
static void services_init(void)
{}
// !!! - 16JAN2015, GWA - FUNCTION ADDED TO SUPPORT BATTERY MONITOR SERVICE
/**************************************************************/
/* Function:   on_bas_evt                              */
/* Description: Called for all Battery Service events that are passed   */
/*             to the application.                     */
/* Parameters: p_bas Battery Service structure.        */
/*             p_evt Event received from the Battery Service.   */
/* Return:    None                                    */
/**************************************************************/
```

```c
static void on_bas_evt(ble_bas_t * p_bas, ble_bas_evt_t *p_evt)
{}
/**@brief Function for handling the Connection Parameters Module.
 *
 * @details This function will be called for all events in the Connection Parameters Module which
 *          are passed to the application.
 *          @note All this function does is to disconnect. This could have been done by simply
 *                setting the disconnect_on_fail config parameter, but instead we use the event
 *                handler mechanism to demonstrate its use.
 *
 * @param[in]   p_evt   Event received from the Connection Parameters Module.
 */
static void on_conn_params_evt(ble_conn_params_evt_t * p_evt)
{}
/**@brief Function for handling a Connection Parameters error.
 *
 * @param[in]   nrf_error   Error code containing information about what went wrong.
 */
static void conn_params_error_handler(uint32_t nrf_error)
{}
/**@brief Function for initializing the Connection Parameters module.
 */
static void conn_params_init(void)
{}
/**@brief Function for starting timers.
 */
static void timers_start(void)
{}
/**@brief Function for starting advertising.
 */
static void advertising_start(void)
{}
/**@brief Function for handling the Application's BLE Stack events.
 *
 * @param[in]   p_ble_evt   Bluetooth stack event.
 */
static void on_ble_evt(ble_evt_t * p_ble_evt)
{}
/**@brief Function for dispatching a BLE stack event to all modules with a BLE stack event handler.
 *
 * @details This function is called from the scheduler in the main loop after a BLE stack
 *          event has been received.
 *
 * @param[in]   p_ble_evt   Bluetooth stack event.
 */
static void ble_evt_dispatch(ble_evt_t * p_ble_evt)
{}
```

```
/**@brief Function for dispatching a system event to interested modules.
 *
 * @details This function is called from the System event interrupt handler after a system
 *          event has been received.
 *
 * @param[in]   sys_evt   System stack event.
 */
static void sys_evt_dispatch(uint32_t sys_evt)
{}
/**@brief Function for initializing the BLE stack.
 *
 * @details Initializes the SoftDevice and the BLE event interrupt.
 */
static void ble_stack_init(void)
{}
/**@brief Function for the Event Scheduler initialization.
 */
static void scheduler_init(void)
{}
static void button_event_handler(uint8_t pin_no, uint8_t button_action)
{}
/*************************************************************/
/* Function:    SetDeviceInd                                 */
/* Description: Sets indication via unit LEDs                */
/* Parameters:  indication - Function/state the indication represents.  */
/* Return:      None                                         */
/*************************************************************/
void SetDeviceInd (device_ind_t indication)
{}
/**@brief Function for initializing the GPIOTE handler module.
 */
static void gpiote_init(void)
{}
/**@brief Function for initializing the button handler module.
 */
static void buttons_init(void)
{}
/*************************************************************/
/* Function:    HeaterOn                                     */
/* Description: Turn on chamber heat.                        */
/* Parameters:  None                                         */
/* Return:      None                                         */
/*************************************************************/
void HeaterOn ( void )
{}
/*************************************************************/
/* Function:    HeaterOff                                    */
```

```
/* Description: Turn off chamber heat.                    */
/* Parameters: None                                       */
/* Return:     None                                       */
/************************************************************/
void HeaterOff ( void )
{}
/************************************************************/
/* Function:   HeatSet                                    */
/* Description: Set chamber heat level.                   */
/* Parameters: None                                       */
/* Return:     None                                       */
/************************************************************/
void HeatSet ( heat_level_t setting )
{}
/************************************************************/
/* Function:   draw_heat_timeout_handler                  */
/* Description: Called when draw heat timer expires.      */
/*              Sets heat level to extended-draw setting. */
/* Parameters: p_context - Pointer used for passing some arbitrary */
/*              information (context) from the app_start_timer() */
/*              call to the timeout handler.              */
/* Return:     None                                       */
/************************************************************/
static void draw_heat_timeout_handler(void * p_context)
{}
/************************************************************/
/* Function:   EvokeInit                                  */
/* Description: Initializes Evoke app operational components. */
/* Parameters: None                                       */
/* Return:     None                                       */
/************************************************************/
void EvokeInit(void)
{}
/************************************************************/
/* Function:   ActivityTOHandler                          */
/* Description: Puts the unit back to sleep when there's not activity. */
/* Parameters: p_context - Pointer used for passing some arbitrary */
/*              information (context) from the app_start_timer() */
/*              call to the timeout handler.              */
/* Return:     None                                       */
/************************************************************/
void ActivityTOHandler( void * p_context )
{}
/************************************************************/
/* Function:   EvokeSetState                              */
/* Description: Sets the Evoke device operating state.    */
/* Parameters: State - Device operating state.            */
```

```
/* Return:    None                              */
/******************************************************************/
void EvokeSetState (device_state_t state)
{}
// !!! - 05MAY2015, GWA - REPLACING START-UP ONLY ACTION/HANDLER WITH STATE HANDLER TO PROCESS
//            ALL BUTTON ACTIONS
/******************************************************************/
/* Function:  EvokeStateHandler                 */
/* Description: Handler to monitor user button inputs to effect device state */
/*           transitions.                       */
/* Parameters: p_context - Pointer used for passing some arbitrary  */
/*             information (context) from the app_start_timer() */
/*             call to the timeout handler.     */
/* Return:    None                              */
/******************************************************************/
void EvokeStateHandler (void * p_context)
{}
void EvokeSleep( void )
{}
/**@brief Function for the Power manager.
 */
static void power_manage(void)
{}
/******************************************************************/
/* Function:  wdt_init                          */
/* Description: Initializes the watchdog timer. */
/* Parameters: None                             */
/* Return:    None                              */
/******************************************************************/
void wdt_init(void)
{}
// !!! - 05MAY2015, GWA - ADDED DEDICATED RUN TIMER
/******************************************************************/
/* Function:  RunTimerInit                      */
/* Description: Initialize dedicated run timer. */
/* Parameters: None                             */
/* Return:    None                              */
/******************************************************************/
static void RunTimerInit(void)
{}
/******************************************************************/
/* Function:  RunTimerStart                     */
/* Description: Sets up and starts the dedicated run timer. */
/* Parameters: None                             */
/* Return:    None                              */
/******************************************************************/
void RunTimerStart (void)
```

```
{}
/******************************************************************/
/* Function:    RunTimerStop                                      */
/* Description: Stops the dedicated run timer.                    */
/* Parameters:  None                                              */
/* Return:      None                                              */
/******************************************************************/
void RunTimerStop (void)
{}
/******************************************************************/
/* Function:    RUN_TIMER_IRQHandler                              */
/* Description: Handlers timer 1 peripheral interrupts.           */
/* Parameters:  None                                              */
/* Return:      None                                              */
/******************************************************************/
void RUN_TIMER_IRQHandler(void)
{}
uint32_t RunTimeGet (void)
{}
/******************************************************************/
/* Function:    CheckOscStart                                     */
/* Description: Tests that the oscillator has started.            */
/* Parameters:  None                                              */
/* Return:      None                                              */
/******************************************************************/
void CheckOscStart( void )
{}
/******************************************************************/
/* Function:    osc_start_timeout_handler                         */
/* Description: Called when heat oscillator startup timer expires.*/
/*              checks that oscillator is oscillating.            */
/* Parameters:  p_context - Pointer used for passing some arbitrary */
/*              information (context) from the app_start_timer()  */
/*              call to the timeout handler.                      */
/* Return:      None                                              */
/******************************************************************/
static void osc_start_timeout_handler(void * p_context)
{}
/******************************************************************/
/* Function:    CheckTOLStart                                     */
/* Description: Initiates detection of thermal overload in the power supply. */
/* Parameters:  None                                              */
/* Return:      None                                              */
/******************************************************************/
void CheckTOLStart( void )
{}
// !!! - 13APR2015, GWA - ADDED TO SUPPORT POWER SUPPLY THERMAL OVERLOAD SHUTDOWN DETECTION
```

```
/************************************************************/
/* Function:   PwrSupplyTOL_Detect                          */
/* Description: The step-up voltage regulator increasingly draws more current */
/*           as the battery discharges.  This causes the device to heat   */
/*           and shutdown due to thermal overload.  The supply          */
/*           subsequently turns back on until thermal overload is reached */
/*           again.  In operation this appears as an oscillation in the  */
/*           supply voltage as the regulator repeatedly cycles on/off.   */
/*           This detection method employs LPCOMP to detect oscillations */
/*           in supply voltage while the oscillator is switched on.      */
/*           An excessive number of oscillations is indicative of thermal */
/*           overload.                                      */
/* Parameters: None                                         */
/* Return:    None                                          */
/************************************************************/
void PwrSupplyTOL_Detect( void )
{}
// !!! - 25MAR2015, GWA - OBSOLETE, ABANDONED LPCOMP BASED OSCILLATOR STARTUP DETECTION
//         CODE RETAINED IN CASE WE NEED TO MAKE USE OF LPCOMP ELSEWHERE
/************************************************************/
/* Function:   LPCOMP_Init                                  */
/* Description: Initialize Low Power Comparitor (LPCOMP) heat Oscillator  */
/*           voltage detection.                             */
/* Parameters: None                                         */
/* Return:    None                                          */
/************************************************************/
void LPCOMP_Init ( void )
{}
//
// !!! - 25MAR2015, GWA - OBSOLETE, ABANDONED LPCOMP BASED OSCILLATOR STARTUP DETECTION
//         CODE RETAINED IN CASE WE NEED TO MAKE USE OF LPCOMP ELSEWHERE
/************************************************************/
/* Function:   LPCOMP_Disable                               */
/* Description: Disable Low Power Comparitor so ADC can use resources.   */
/* Parameters: None                                         */
/* Return:    None                                          */
/************************************************************/
void LPCOMP_Disable ( void )
{}
//
// !!! - 25MAR2015, GWA - OBSOLETE, ABANDONED LPCOMP BASED OSCILLATOR STARTUP DETECTION
//         CODE RETAINED IN CASE WE NEED TO MAKE USE OF LPCOMP ELSEWHERE
/************************************************************/
/* Function:   LPCOMP_IRQHandler                            */
/* Description: Handle Low Power Comparitor interrupt event.             */
/* Parameters: None                                         */
/* Return:    None                                          */
```

```
/*************************************************************/
void LPCOMP_IRQHandler(void)
{}
/* !!!- 16MAR2015, GWA - ALTERNATIVE BUTTON HANDLER          */

/*************************************************************/
/* Function:    Alt_ButtonInit                               */
/* Description: Initialize buttons for alternative button handler. */
/* Parameters:  None                                         */
/* Return:      None                                         */
/*************************************************************/
void Alt_ButtonInit ( void )
{}
/*************************************************************/
/* Function:    Alt_ButtonTOHandler                          */
/* Description: Called when button poll timer expires.       */
/*              Checks for button state transitions.         */
/* Parameters:  p_context - Pointer used for passing some arbitrary */
/*              information (context) from the app_start_timer() */
/*              call to the timeout handler.                 */
/* Return:      None                                         */
/*************************************************************/
static void Alt_ButtonTOHandler ( void * p_context)
{}
/*************************************************************/
/* Function:    Alt_ButtonHandler                            */
/* Description: Checks and maintains debounced button state. */
/* Parameters:  None                                         */
/* Return:      None                                         */
/*************************************************************/ void Alt_ButtonHandler ( void )
{}
/*************************************************************/
/* Function:    conv_temp                                    */
/* Description: Converte ADC reading into temperature.       */
/* Parameters:  None                                         */
/* Return:      None                                         */
/*************************************************************/
int16_t conv_temp (uint8_t adcValue)
{}
/*************************************************************/
/*            NVM STORAGE/RETRIEVAL FUNCTIONS                */
/*************************************************************/

/*************************************************************/
/* Function:    NvmParmsInit                                 */
```

```c
/* Description: Initialize NVM for heat profiles storage/retrieval.  */
/* Parameters: None                                                   */
/* Return:    None                                                    */
/********************************************************************/
static void NvmParmasInit( void )
{}

/********************************************************************/
/* Function:   GetHeatProfile                                         */
/* Description: Retrieves stored heat profile from NVM.               */
/* Parameters: None                                                   */
/* Return:    None                                                    */
/********************************************************************/
static void GetHeatProfile ( void )
{}

/********************************************************************/
/* Function:   StoreHeatProfile                                       */
/* Description: Store heat provile in NVM.                            */
/* Parameters: None                                                   */
/* Return:    None                                                    */
/********************************************************************/
static void StoreHeatProfile ( void )
{}
static void nvm_param_cb_handler(pstorage_handle_t  * handle,
                                 uint8_t  op_code,
                                 uint32_t   result,
                                 uint8_t    * p_data,
                                 uint32_t   data_len)
{} ifdef PSTORAGE_TEST_STORE_UPDATE
static void pstorage_test_store_and_update(void)
{
        pstorage_handle_t    handle;
        pstorage_handle_t        block_0_handle;
        pstorage_handle_t          block_1_handle;
        pstorage_handle_t          block_2_handle;
        pstorage_module_param_t param;
        uint8_t      source_data_0[16] = {0x00, 0x01, 0x02, 0x03, 0x04, 0x05, 0x06, 0x07, 0x08, 0x09, 0x0A, 0x0B, 0x0C, 0x0D, 0x0E, 0x0F};
        uint8_t      source_data_1[16] = {0x10, 0x11, 0x12, 0x13, 0x14, 0x15, 0x16, 0x17, 0x18, 0x19, 0x1A, 0x1B, 0x1C, 0x1D, 0x1E, 0x1F};
        uint8_t      source_data_2[16] = {0x20, 0x21, 0x22, 0x23, 0x24, 0x25, 0x26, 0x27, 0x28, 0x29, 0x2A, 0x2B, 0x2C, 0x2D, 0x2E, 0x2F};
```

```
                uint8_t     source_data_9[16] = {0x90, 0x91, 0x92, 0x93, 0x94, 0x95, 0x96, 0x97, 0x98, 0x99,
0x9A, 0x9B, 0x9C, 0x9D, 0x9E, 0x9F};
                uint8_t     dest_data_0[16];
                uint8_t     dest_data_1[16];
                uint8_t     dest_data_2[16];
                uint32_t    retval;

retval = pstorage_init();
                if(retval != NRF_SUCCESS)
                {
//                              nrf_gpio_pin_set(PSTORAGE_ERROR_LED_PIN_NO);
                } param.block_size = 16;          //Select block size of 16 bytes
                param.block_count = 10;         //Select 10 blocks, total of 160 bytes
                param.cb       = example_cb_handler;   //Set the pstorage callback handler retval = pstorage_register(¶m, &handle);
                if (retval != NRF_SUCCESS)
                {
//                              nrf_gpio_pin_set(PSTORAGE_ERROR_LED_PIN_NO);
                }

//Get block identifiers
                pstorage_block_identifier_get(&handle, 0, &block_0_handle);
                pstorage_block_identifier_get(&handle, 1, &block_1_handle);
                pstorage_block_identifier_get(&handle, 2, &block_2_handle);

pstorage_clear(&block_0_handle, 48);          //Clear 48 bytes

//Store data to three blocks. Wait for the last store operation to finish before reading out the data.
                pstorage_store(&block_0_handle, source_data_0, 16, 0);   //Write to flash, only one block is allowed
for each pstorage_store command
                pstorage_store(&block_1_handle, source_data_1, 16, 0);   //Write to flash, only one block is allowed
for each pstorage_store command
                pstorage_wait_handle = block_2_handle.block_id;          //Specify which pstorage handle to wait for
                pstorage_wait_flag = 1;                                  //Set the wait flag. Cleared in the example_cb_handler pstorage_store(&block_2_handle, source_data_2, 16, 0);   //Write to flash
/*
    //Sleep until store operation is finished.
                while(pstorage_wait_flag)
    {
      power_manage();
    }
```

```
            pstorage_load(dest_data_0, &block_0_handle, 16, 0);                    //Read
from flash, only one block is allowed for each pstorage_load command
            pstorage_load(dest_data_1, &block_1_handle, 16, 0);                    //Read
from flash
            pstorage_load(dest_data_2, &block_2_handle, 16, 0);                    //Read from flash pstorage_wait_handle = block_0_handle.block_id;    //Specify which pstorage handle to wait for
            pstorage_wait_flag = 1;                            //Set the wait flag. Cleared in the example_cb_handler
            pstorage_clear(&block_0_handle, 32);               //Clear 32 bytes
            while(pstorage_wait_flag);// { power_manage(); }   //Sleep until store operation is finished.

pstorage_load(dest_data_0, &block_0_handle, 16, 0);                    //Read
from flash, only one block is allowed for each pstorage_load command
            pstorage_load(dest_data_1, &block_1_handle, 16, 0);                    //Read
from flash
            pstorage_load(dest_data_2, &block_2_handle, 16, 0);                    //Read from flash pstorage_wait_handle = block_0_handle.block_id;    //Specify which pstorage handle to wait for
            pstorage_wait_flag = 1;                            //Set the wait flag. Cleared in the example_cb_handler
            pstorage_update(&block_0_handle, source_data_9, 16, 0);   //update flash block 0
            while(pstorage_wait_flag);// { power_manage(); }   //Sleep until update operation is finished.

pstorage_load(dest_data_0, &block_0_handle, 16, 0);                    //Read
from flash, only one block is allowed for each pstorage_load command
            pstorage_load(dest_data_1, &block_1_handle, 16, 0);                    //Read
from flash
            pstorage_load(dest_data_2, &block_2_handle, 16, 0);                    //Read from flash
    */
}
endif //PSTORAGE_TEST_STORE_UPDATE /**@brief Function for application main entry.
 */
int main(void)
{
  // Initialize
  timers_init();
  gpiote_init();
//
// !!! - 06APR2015, GWA - ADDED TO SUPPORT SEGGER RTT LOGGING
  // For errors use: loge("!!! ASSSERT ERROR: %d", s_error_code)
  // For warnings use: logw(""Warning: Something")
  // For information use: logi("Info: (%d)", infoValue)

SEGGER_RTT_ConfigUpBuffer(0, NULL, NULL, 0, SEGGER_RTT_MODE_BLOCK_IF_FIFO_FULL);
  SEGGER_RTT_WriteString(0, "SEGGER Real-Time-Terminal Start\r\n\r\n");
  SEGGER_RTT_WriteString(0, "###### Testing SEGGER_printf() ######\r\n");
```

```
// !!! - 06MAY2015, GWA - REINSTATED ORIGINAL BUTTON PRESS
// !!! - 16MAR2015, GWA - REM'D AND REPLACED BY ALT BUTTON HANDLER DEV CODE
//   Alt_ButtonInit();
   buttons_init();

ble_stack_init();
   scheduler_init();
   gap_params_init();

// !!! - 01APR2015, GWA - ADD NVM INIT, CHECK AND UPDATE NVM STORED VARIABLES
   NvmParmasInit();

services_init();
   advertising_init();
   conn_params_init();
   sec_params_init();

leds_init();

// Init device
   EvokeInit();

// Start execution
   timers_start();
   advertising_start();

// Configure and enable the watchdog timer
   wdt_init();

// !!! - 27MAR2015, GWA - ADDED FOR DEVELOPING NVM STORAGE AND RETRIEVAL
#ifdef PSTORAGE_TEST_STORE_UPDATE
                pstorage_test_store_and_update();
endif // Enter main loop
   for (;;)
   {
      // Run scheduler and execute queued events
      app_sched_execute();

// Manage power
      power_manage();

// Clear the watchdog timer
      NRF_WDT->RR[0] = WDT_RR_RR_Reload;   //Reload watchdog register 0
   }
}
```

In additional embodiments, the firmware may perform one or all of the following functions:

- In the draw cycle perform the following sequence: Sense the temperature category of vaping material and possibly the specific compound being vaporized (if this is encoded on the cartridge) and use these together with a look-up-table of settings relevant to that temperature and material to select heat cycle settings. Use maximum power for a short pulse (the pulse time from the look-up-table) to get the material to vaping temperature as quickly as possible. Reduce the heating power to a steady state level, again supplied by the look up table while the button is held down. Record the energy that has been delivered to the coil and use this together with a temperature cool down model to modify the look-up-table as time progresses until the next press of the button for a draw cycle. (The model may be a simple exponential decay of temperature over time)
- Allow the user to swap between a number of look-up-tables that change the quality of the vaping experience or the are optimized for vaping different materials. For example one look-up-table may be optimized to produce large clouds of vapor while another may be optimized to prolong battery life and yet another to work with a novel material such as a nicotine containing wax.
- Sense and report the state of the battery charge using the feedback LEDs.
- Replace itself with a new version of the firmware that would be downloaded from a repository maintained on the internet.
- Connect via Bluetooth to a host computer or smartphone and upload usage data that may be of use to the user (such as nicotine intake or medical marijuana dose where it is legal) or may be of use to the manufacturer to gain an understanding of the consumer use cases an example of which is to determine battery life.

Figure 16:
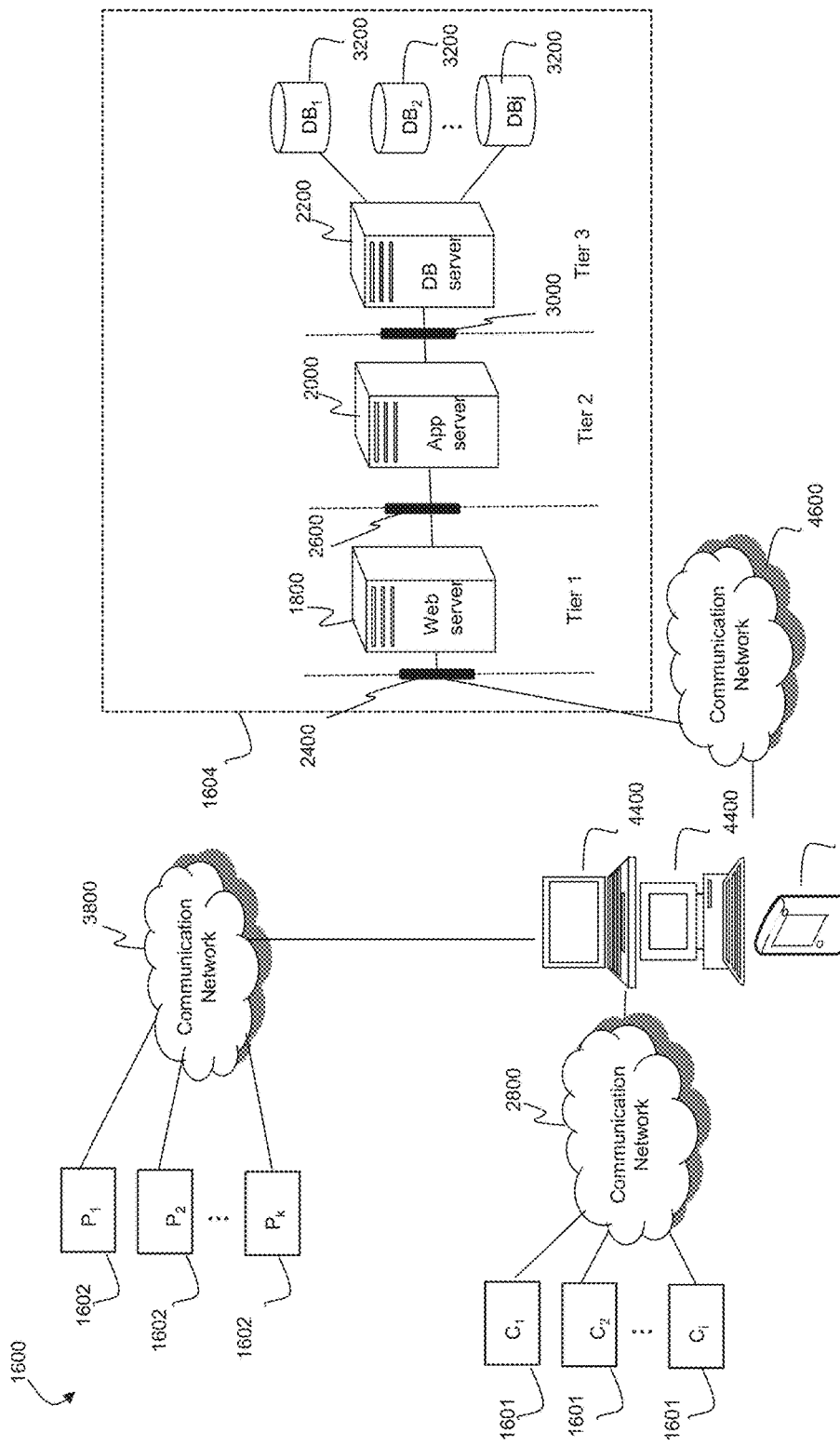
FIG. 16 depicts example network architecture and computing environment for various embodiments of the present disclosure

FIG. 16 illustrates a network architecture and computing environment for an embodiment of a system 1600 that communicates with a vaporizer device or vaporizer devices as disclosed herein. FIG. 16 illustrates system 1600 according to embodiments of the present disclosure. As shown in FIG. 16, the system 1600 includes one or more client devices C1, C2, . . . , Ci 1601 (hereinafter referred to as "clients 1601") in communication with one or more remote computing devices 4400 via a communications network 2800 and the computing devices 4400 are in communication with a host system 1604 via a communications network 4600. In embodiments, additional clients P1, P2, . . . , Pk 1602 (hereinafter referred to as "clients 1602") are in communication with the computing devices 4400 via a communications network 3800. The communication networks 2800, 3800, and 4600 may be a common communication network (e.g., the Internet). In certain embodiments, the host system 1604 and/or the computing devices 4400 may implement some or all of the aspects of a central monitoring and control system, respectively, and the clients 1601, 1602 may implement some or all of the aspects of the vaporizer device described herein. The system 1600 may allow users of vaporizer device to communicate with other users to share experience and knowledge of their devices, may allow for firmware/software updates to devices, and/or may allow third parties to monitor the usage of vaporizer devices for certain substances that constitute vaporizable substances to be used with a vaporizer device.

While the communications networks 2800, 3800, and 4600 may be the Internet, it will be appreciated that any public or private communication network, using wired or wireless channels, suitable for enabling the electronic exchange of information between the clients 1601, clients 1602, the computing devices 4400, and the host system 1604 may be utilized. The one or more of the communications networks 2800, 3800 and 4600 can be any network or combination of networks that can carry data communications. Such networks can include, but are not limited to, wireless data networks such as a Wi-Fi, 3G, and a 4G/LTE network. In addition, the communications networks 2800, 3800, and 4600 shown in FIG. 16 can include, but are not limited to a wired Ethernet network, a local area network (LAN), a medium area network, and/or a wide area network (WAN) such as the Internet. In various implementations of system 1000 including wireless networks, one or more of the communications networks 2800, 3800 and 4600 can support protocols and technology including, but not limited to, Internet or World Wide Web protocols and/or services. Intermediate network routers, gateways, or servers (not shown) may be provided between components of the system 1600 depending upon a particular application or environment.

According to various embodiments, the host system 1604 may be implemented by an institution, (hereinafter referred to as a 'host institution') such as for example, a doctor's office that provides services to a user of a vaporizer device, where the vaporizer device is used in conjunction with vaporizable substance that is a medicine, such as medicinal marijuana. In additional embodiments, the functional aspects of the computing devices 4400 can be included within the host system 1604, and the clients 1601, 1602 communicate with, provide information to, and receive commands from the host system 1604, directly. In addition, the host institution may be in the form of a hospital, care provider, or other form of medical service provider.

In preferred embodiments, the clients 1601, 1602 may include any form of network-enabled communications module configured to transmit and receive information via the communications networks 2800, 3800 using a wired or wireless connection. Clients 1601, 1602 are capable of receiving user input from the computing devices 4400 via the communications networks 2800, 3800. In various embodiments, a computing device 4400 can be, but is not limited to, a personal computer (PC), may be PCs and/or other network-enabled devices (e.g., cell phones, mobile phones, mobile tablets, PDAs, etc.) configured to transmit and receive information via the communication networks 2800, 3800, 4600 using a wired or wireless connection. Furthermore, the computing devices 4400 may be an iPhone™, an iPod™, an iPad™, a device operating the Android operating system ("OS") from Google Inc., a device running the Microsoft Windows® Mobile OS, a device running the Microsoft Windows® Phone OS, a device running the Symbian OS, a device running the webOS from Hewlett Packard, Inc., a mobile phone, a BlackBerry® device, a smartphone, a hand held computer, a netbook computer, a palmtop computer, a laptop computer, an ultra-mobile PC, a portable gaming system, or another similar type of mobile computing device having a capability to communicate with clients 1601, 1602 and the host system 1604 via the communications networks 2800, 3800, 4600. The computing devices 4400 may include a suitable browser software application (e.g., Internet Explorer, Internet Explorer Mobile, Chrome, Safari, Firefox, Blazer, etc.) for enabling the user to display and interact with information exchanged via the communication networks 2800, 3800, 4600.

According to embodiments, an input device of the computing device 4400 may be one or more of a touch-sensitive display such as a touch screen interface, a keyboard, a microphone, or a pointing device such as a mouse or stylus. The computing device 4400 also include a display device capable of rendering an interactive Graphical User Interface ("GUI") for providing commands to the clients 1601, 1602. The input device allows a user to interact with the GUI to instruct the clients 1601, 1602 and to display and edit information, which is rendered in the display device. The computing devices 4400 may thus access and navigate static and/or dynamic HTML documents of the GUI. Alternatively, the GUI can be rendered on a display device of one or more servers, such as a web server 1800, application server 2000, and database server 2200 shown in FIG. 16.

A display device of the computing device 4400 can differ depending on the application of the vaporizer device. For example, a display device of a tablet device, netbook, or laptop is typically an integrated LCD screen, which is often smaller than a monitor or console such as the display device for a workstation or desktop PC. Similarly, the display device of a mobile computing device may be a relatively small display such as mobile phone display.

The input devices can also vary depending on the characteristics of a particular computing device 4400 and its display device. For example, the input device of a tablet, netbook, or laptop may include a relatively small physical or touchscreen keyboard, an integrated camera, track pad, and/or microphone, while the input device of a desktop PC or workstation client will typically include a physical QWERTY or Dvorak keyboard and a mouse. Also, for example, an input device of a mobile device will typically lack a full physical keyboard and may instead comprise one or more of a touch-screen keyboard, a microphone, an integrated camera, a track pad, a scroll wheel, a track ball, a T9 keyboard, a button, and a touch screen display device. In embodiments, a display device can be a touch screen display. It is to be understood that in the case of a touch screen interface, the input device can be anything capable of interacting with the touch screen, including a user's fingers, which can be used to select, slide, drag, and resize (i.e., expand, maximize, shrink, and/or minimize) interactive user interface ("UI") elements through pointing, pinching, and scrolling gestures.

According to embodiments, UIs for mobile computing devices may be rendered as streamlined 'mobile friendly' versions of the 'full' UI for ease of use on relatively small display devices. In embodiments, mobile friendly UIs may have reduced capabilities and/or display a lesser level of detail as compared to full UI. A mobile friendly UI can also be tailored to accept input from input devices for a specific platform of a mobile computing device. Mobile friendly UIs can be automatically selected by the system 1600 in response to detecting one or more platform characteristics of a particular mobile computing device. Alternatively, a user of a mobile computing device can be prompted within the full UI to opt-in to using the mobile friendly UIs in response to detecting that the computing device is accessing the host system 1604 via a mobile computing device. In cases where a user's mobile computing device has display devices and input devices capable of using the full UI, the user may not wish to use the mobile friendly UI.

In accordance with embodiments, the UI can be tailored to or customized for a particular computing device 4400 based on the capabilities of the platform used by that computing device. The platform comprises physical capabilities of the computing device such as, memory capacity in terms of random access memory (RAM) and read only memory (ROM), central processing unit (CPU) capabilities in terms of clock speed and available processing capacity, available storage in terms of disk space or flash memory, communications capabilities in terms of current wired and/or wireless network connectivity and a communications interface such as a network interface card ("NIC") of the computing device, capabilities of the display device, and capabilities of the input device. These physical capabilities and others can be determined based on a manufacturer, model number, serial number, a Media Access Control address ("MAC address") and/or another unique identifier of a computing device 4400.

The platform of a computing device 4400 also comprises software and firmware components, such as an operating system ("OS") running on the computing device 4400, Internet browser(s), native software applications installed, and privileges/permissions associated with the computing device. The privileges/permissions may be controlled by the host system 1604 based on a user and/or an entity associated with the computing device and can include data access, communications, and application execution privileges.

In the embodiment depicted in FIG. 16, the host system 1604 can be based on a multi-tiered network architecture, and can include one or more of a web server 1800 (Tier 1), an application server 2000 (Tier 2), and a database server 2200 (Tier 3). According to this embodiment, the web server 1800 corresponds to the first tier of the host system 1604 and is configured to communicate with the communication network 4600 via a border firewall 2400, and with the application server 2000 via an application firewall 2600. The web server 1800 can be configured to accept information requests, such as, for example, HTTP requests, from one or more of the computing devices 4400 via the communication network 4600 and to provide responses thereto. The responses may include, for example, HTTP responses including static and/or dynamic HTML documents for providing a GUI to users via the computing devices 4400. Additionally, the web server 1800 may further be configured to authenticate each user before allowing access to a GUI and other resources associated with the host system 1604. Authentication may be performed, for example, by validating a received account identifier ("ID") or user name and a corresponding password. The ID/user name and password may be input in the GUI using an input device of the computing device 4400.

With continued reference to the embodiment of FIG. 16, the application server 2000 corresponds to the second tier of the host system 1604 and can be configured to communicate with the web server 1800 via the application firewall 2600, and with the database server 2200 via an internal firewall 3000. The application server 2000 may host one or more applications executing logic to provide features to each user of a vaporizer device via a respective user interface ("UI"). The application server 3000 may receive account credentials (e.g., an account ID/user name and password), input and selections (e.g., a request to access data management features) from the UI associated with each client 1601, 1602 via the web server 1800. Based on this and other information received from the clients 1601, 1602 applications hosted by the application server 2000 may be invoked to perform various calculations or data manipulation functions and generate corresponding informational content. Informational content may be communicated to the web server 1800 and subsequently presented to a user associated with computing, device 4400 using, for example, a dynamic web page or interactive GUI. Additionally, the application server 2000 may also host an application for enabling users to conduct email communication with the parties associated with the host system 1604 and other parties, for example maintenance contractors based on alerts or other informational content associated with the system 1600.

In the embodiment shown in FIG. 16, the database server 2200 corresponds to the third tier of the host system 1604 and is configured to communicate with the application server 2000 via the internal firewall 3000. The database server 2200 manages one or more databases DB1, DB2, . . . , DBi 3200 (hereinafter referred to as "databases 3200") which store data to support one or more applications hosted by the application server 2000 or elsewhere. Such databases may include, for example, stored information databases, client configuration databases, user reporting databases, user identification/authentication databases, user preferences/settings databases, as well as databases for storing other settings and/or configuration data. Database information requested by a particular application is retrieved from the databases 3200 by the database server 2200, communicated to the requesting application, and updated by the database server 2200 as needed. Additionally, although only a web server 1800, application server 2000, and database server 2200 are depicted in FIG. 16, it is to be understood that in certain embodiments, the functionalities of one or more of these servers can be implemented cluster of computing devices operating in a cluster or server farm.

As would be appreciated by someone skilled in the relevant art(s) and described below with reference to FIG. 17, part or all of one or more aspects of the methods and system discussed herein may be distributed as an article of manufacture that itself comprises a computer readable medium having computer readable code means embodied thereon.

The computer readable program code means is operable, in conjunction with a computer system, to carry out all or some of the steps to perform the methods or create the system discussed herein. The computer readable medium may be a recordable medium (e.g., hard drives, compact disks, EPROMs, or memory cards). Any tangible medium known or developed that can store information suitable for use with a computer system may be used. The computer-readable code means is any mechanism for allowing a computer to read instructions and data, such as magnetic variations on a magnetic media or optical characteristic variations on the surface of a compact disk. The medium can be distributed on multiple physical devices (or over multiple networks). For example, one device could be a physical memory media associated with a terminal and another device could be a physical memory media associated with a processing center.

The computer devices, systems, and servers described herein each contain a memory that will configure associated processors to implement the methods, steps, and functions disclosed herein. Such methods, steps, and functions can be carried out, e.g., by processing capability on mobile device, POS terminal, payment processor, acquirer, issuer, or by any combination of the foregoing. The memories could be distributed or local and the processors could be distributed or singular. The memories could be implemented as an electrical, magnetic or optical memory, or any combination of these or other types of storage devices. Moreover, the terms "memory", "memory storage", "memory device", or similar terms should be construed broadly enough to encompass any information able to be read from or written to an address in the addressable space accessed by an associated processor.

Aspects of the present disclosure discussed with regards to and shown in FIGS. 1-15, or any part(s) or function(s) thereof as appropriate, may be implemented using hardware, software modules, firmware, tangible computer readable media having instructions stored thereon, or a combination thereof and may be implemented in one or more computer systems or other processing systems.

Figure 17:
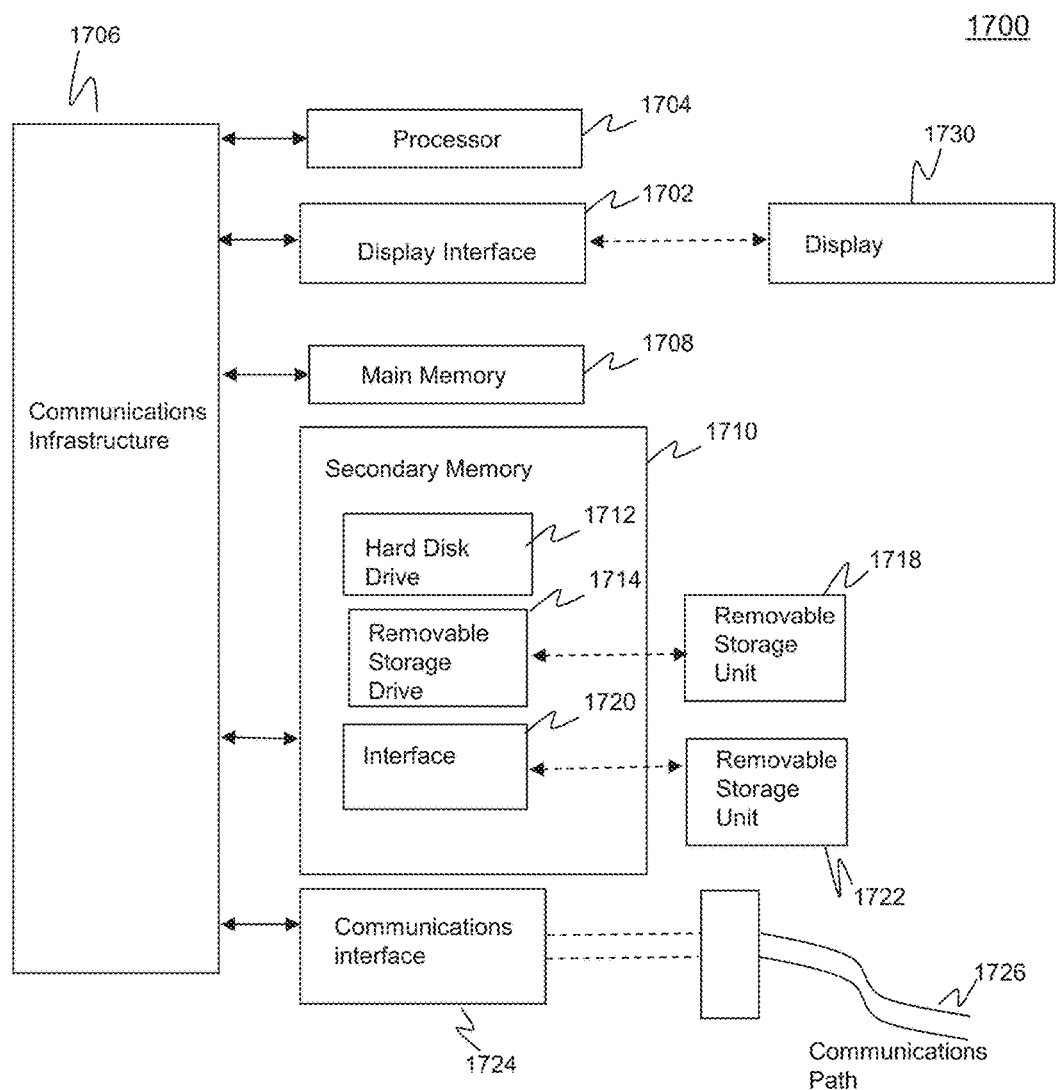
FIG. 17 depicts an example computer system in which embodiments of the present disclosure may be implemented.

FIG. 17 illustrates an example computer system 1700 in which embodiments of the present disclosure, or portions thereof, may be implemented as computer-readable code. For example, the various aspects of the user interface can be implemented in computer system 1700 using hardware, software, firmware, non-transitory computer readable media having instructions stored thereon, or a combination thereof and may be implemented in one or more computer systems or other processing systems. Hardware, software, or any combination of such may embody any of the modules and components used to implement the network, systems, methods and GUI described above. For example, some or all of the aspects, as appropriate, of the computing devices 4400, web server 1800, application server 2000, and/or database server 2200 described above with reference to FIG. 16 can be implemented using computer system 1700.

If programmable logic is used, such logic may execute on a commercially available processing platform or a special purpose device. One of ordinary skill in the art may appreciate that embodiments of the disclosed subject matter can be practiced with various computer system configurations, including multi-core multiprocessor systems, minicomputers, mainframe computers, computers linked or clustered with distributed functions, as well as pervasive or miniature computers that may be embedded into virtually any device. For instance, at least one processor device and a memory may be used to implement the above described embodiments. A processor device may be a single processor, a plurality of processors, or combinations thereof. Processor devices may have one or more processor "cores."

Various embodiments of the present disclosure are described in terms of this example computer system 1700. After reading this description, it will become apparent to a person skilled in the relevant art how to implement the present disclosure using other computer systems and/or computer architectures. Although operations may be described as a sequential process, some of the operations may in fact be performed in parallel, concurrently, and/or in a distributed environment, and with program code stored locally or remotely for access by single or multiprocessor machines. In addition, in some embodiments the order of operations may be rearranged without departing from the spirit of the disclosed subject matter.

The processor device 1704 may be a special purpose or a general purpose processor device. As will be appreciated by persons skilled in the relevant art, processor device 1704 may also be a single processor in a multi-core/multiprocessor system, such system operating alone, or in a cluster of computing devices operating in a cluster or server farm. Processor device 1704 is connected to a communication infrastructure 1706, for example, a bus, message queue, network, or multi-core message-passing scheme.

The computer system 1700 also includes a main memory 1708, for example, random access memory (RAM), and may also include a secondary memory 1710. Secondary memory 1710 may include, for example, a hard disk drive 1712, removable storage drive 1714. Removable storage drive 1714 may comprise a floppy disk drive, a magnetic tape drive, an optical disk drive, a flash memory, or the like.

The removable storage drive 1714 may read from and/or writes to a removable storage unit 1718 in a well-known manner. The removable storage unit 1718 may comprise a floppy disk, magnetic tape, optical disk, Universal Serial Bus ("USB") drive, flash drive, memory stick, etc. which is read by and written to by removable storage drive 1714. As will be appreciated by persons skilled in the relevant art, the removable storage unit 1718 includes a non-transitory computer usable storage medium having stored therein computer software and/or data.

In alternative implementations, the secondary memory 1710 may include other similar means for allowing computer programs or other instructions to be loaded into computer system 1700. Such means may include, for example, a removable storage unit 1722 and an interface 1720. Examples of such means may include a program cartridge and cartridge interface (such as that found in video game devices), a removable memory chip (such as an EPROM, or PROM) and associated socket, and other removable storage units 1722 and interfaces 1720 which allow software and data to be transferred from the removable storage unit 1722 to computer system 1700.

The computer system 1700 may also include a communications interface 1724. The communications interface 1724 allows software and data to be transferred between the computer system 1700 and external devices. The communications interface 1724 may include a modem, a network interface (such as an Ethernet card), a communications port, a PCMCIA slot and card, or the like. Software and data transferred via the communications interface 1724 may be in the form of signals, which may be electronic, electromagnetic, optical, or other signals capable of being received by communications interface 1724. These signals may be provided to the communications interface 1724 via a communications path 1726. The communications path 1726 carries signals and may be implemented using wire or cable, fiber optics, a phone line, a cellular/wireless phone link, an RF link or other communications channels.

In this document, the terms 'computer readable storage medium,' 'computer program medium,' 'non-transitory computer readable medium,' and 'computer usable medium' are used to generally refer to tangible and non-transitory media such as removable storage unit 1718, removable storage unit 1722, and a hard disk installed in hard disk drive 1712. Signals carried over the communications path 1726 can also embody the logic described herein. The computer readable storage medium, computer program medium, non-transitory computer readable medium, and computer usable medium can also refer to memories, such as main memory 1708 and secondary memory 1710, which can be memory semiconductors (e.g. DRAMs, etc.). These computer program products are means for providing software to computer system 1700. Computer programs (also called computer control logic and software) are generally stored in a main memory 1708 and/or secondary memory 1710. The computer programs may also be received via a communications interface 1724. Such computer programs, when executed, enable computer system 1700 to become a specific purpose computer able to implement the present disclosure as discussed herein. In particular, the computer programs, when executed, enable the processor device 1704 to implement the processes of the present disclosure discussed below. Accordingly, such computer programs represent controllers of the computer system 1700. Where the present disclosure is implemented using software, the software may be stored in a computer program product and loaded into the computer system 1300 using the removable storage drive 1714, interface 1720, and hard disk drive 1712, or communications interface 1724.

The functions of the various functional elements, logical blocks, modules, and circuits elements described in connection with the embodiments disclosed herein may be implemented in the general context of computer executable instructions, such as software, control modules, logic, and/or logic modules executed by the processing unit. Generally, software, control modules, logic, and/or logic modules comprise any software element arranged to perform particular operations. Software, control modules, logic, and/or logic modules can comprise routines, programs, objects, components, data structures and the like that perform particular tasks or implement particular data types. An implementation of the software, control modules, logic, and/or logic modules and techniques may be stored on and/or transmitted across some form of computer-readable media. In this regard, computer-readable media can be any available medium or media useable to store information and accessible by a computing device. Some embodiments also may be practiced in distributed computing environments where operations are performed by one or more remote processing devices that are linked through a communications network. In a distributed computing environment, software, control modules, logic, and/or logic modules may be located in both local and remote computer storage media including memory storage devices.

Additionally, it is to be appreciated that the embodiments described herein illustrate example implementations, and that the functional elements, logical blocks, modules, and circuits elements may be implemented in various other ways which are consistent with the described embodiments. Furthermore, the operations performed by such functional elements, logical blocks, modules, and circuits elements may be combined and/or separated for a given implementation and may be performed by a greater number or fewer number of components or modules. As will be apparent to those of skill in the art upon reading the present disclosure, each of the individual embodiments described and illustrated herein has discrete components and features which may be readily separated from or combined with the features of any of the other several embodiments without departing from the scope of the present disclosure. Any recited method can be carried out in the order of events recited or in any other order which is logically possible.

It is worthy to note that any reference to "one embodiment" or "an embodiment" means that a particular feature, structure, or characteristic described in connection with the embodiment is comprised in at least one embodiment of the present disclosure. The appearances of the phrase "in one embodiment" or "in one embodiment" in the specification are not necessarily all referring to the same embodiment.

Unless specifically stated otherwise, it may be appreciated that terms such as "processing," "computing," "calculating," "determining," or the like, refer to the action and/or processes of a computer or computing system, or similar electronic computing device, such as a general purpose processor, a DSP, ASIC, FPGA or other programmable logic device, discrete gate or transistor logic, discrete hardware components, or any combination thereof designed to perform the functions described herein that manipulates and/or transforms data represented as physical quantities (e.g., electronic) within registers and/or memories into other data similarly represented as physical quantities within the memories, registers or other such information storage, transmission or display devices. Additionally, It is worthy to note that some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, also may mean that two or more elements are not in direct contact with each other, but yet still co-operate or interact with each other. With respect to software elements, for example, the term "coupled" may refer to interfaces, message interfaces, application program interface (API), exchanging messages, and so forth.

It will be appreciated that those skilled in the art will be able to devise various arrangements which, although not explicitly described or shown herein, embody the principles of the present disclosure and are comprised within the scope thereof. Furthermore, all examples and conditional language recited herein are principally intended to aid the reader in understanding the principles described in the present disclosure and the concepts contributed to furthering the art, and are to be construed as being without limitation to such specifically recited examples and conditions. Moreover, all statements herein reciting principles, embodiments, and embodiments as well as specific examples thereof, are intended to encompass both structural and functional equivalents thereof. Additionally, it is intended that such equivalents comprise both currently known equivalents and equivalents developed in the future, i.e., any elements developed that perform the same function, regardless of structure. The scope of the present disclosure, therefore, is not intended to be limited to the exemplary embodiments and embodiments shown and described herein. Rather, the scope of present disclosure is embodied by the appended claims.

The terms "a" and "an" and "the" and similar referents used in the context of the present disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as when it were individually recited herein. All methods described herein can be performed in any suitable order unless otherwise indicated herein or otherwise clearly contradicted by context. The use of any and all examples, or exemplary language (e.g., "such as," "in the case," "by way of example") provided herein is intended merely to better illuminate the disclosed embodiments and does not pose a limitation on the scope otherwise claimed. No language in the specification should be construed as indicating any non-claimed element essential to the practice of the claimed subject matter. It is further noted that the claims may be drafted to exclude any optional element. As such, this statement is intended to serve as antecedent basis for use of such exclusive terminology as solely, only and the like in connection with the recitation of claim elements, or use of a negative limitation.

Groupings of alternative elements or embodiments disclosed herein are not to be construed as limitations. Each group member may be referred to and claimed individually or in any combination with other members of the group or other elements found herein. It is anticipated that one or more members of a group may be comprised in, or deleted from, a group for reasons of convenience and/or patentability.

Although the various embodiments of the devices have been described herein in connection with certain disclosed embodiments, many modifications and variations to those embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Various embodiments are described in the following numbered clauses:

1. A vaporizer device comprising:
    a cartridge configured to hold a vaporizable substance;
    a wick element coupled to the cartridge, wherein the wick element is configured to contact the vaporizable substance located in the cartridge; and
    an induction heating element inductively coupled to the wick element; and
    wherein the wick element is configured to heat the vaporizable substance based on induction heating of the wick element by the induction heating element.

2. The vaporizer device of clause 1, wherein the cartridge comprises a reservoir, and wherein the wick element is configured to transfer the vaporizable substance from the reservoir based on a capillary action of the wick element.

3. The vaporizer device of clause 1, further comprising an insulating member disposed between the wick element and the induction heating element.

4. The vaporizer device of clause 3, wherein the induction heating element comprises an induction coil disposed about the insulating member.

5. The vaporizer device of clause 4, wherein the insulating member defines an inside surface and wherein the wick element is positioned adjacent to the inside surface of the insulating member.

6. The vaporizer device of clause 1, wherein the wick element comprises a magnetic material or a metallic conductor.

7. The vaporizer device of clause 6, wherein the wick element has a material configuration, wherein the material configuration is selected from the group consisting of a mesh, a plurality of strands, or a porous solid material, and any combination thereof.

8. The vaporizer device of clause 1, wherein the vaporizable substance produces a vapor for inhalation by a human being when heated to a predetermined temperature.

9. The vaporizer device of clause 8, wherein the vaporizable substance is selected from the group consisting of a liquid, a wax, or a plant material, and any combination thereof.

10. The vaporizer device of clause 1, further comprising at least one additional heating element.

11. The vaporizer device of clause 10, wherein the at least one additional heating element is a resistive heating element or an induction heating element.

12. The vaporizer device of clause 1, further comprising a processor coupled to the induction heating element, wherein the processor is configured to control operation of the induction heating element.

13. The vaporizer device of clause 12, wherein the processor is programmed to restrict operation of the induction element to a specific user of the vaporizer device.

14. The vaporizer device of clause 12, wherein the processor is programmed to cause the induction heating element to apply a predetermined heating profile to the vaporizable substance.

15. The vaporizer device of clause 14, wherein the predetermined heating profile is based on the vaporizable substance.

16. A vaporizer device comprising:
a chassis; and
an induction heating element located at least partially within the chassis;
wherein the chamber is sized and configured to receive a cartridge within the induction heating element and the chassis;
wherein the induction heating element is configured to heat a vaporizable substance in the cartridge when the cartridge is within the chassis and the heating element is configured to heat the vaporizable substance based on induction heating of the cartridge.

17. The vaporizer device of clause 16, wherein the cartridge comprises a wick element, wherein the wick element is configured to be in contact with the vaporizable substance and to heat the vaporizable substance based on induction heating of the wick element by the induction heating element.

18. The vaporizer device of clause 17, wherein the vaporizable substance is selected from the group consisting of a liquid, a wax, or a plant material, and any combination thereof.

19. The vaporizer device of clause 16, further comprising a processor coupled to the induction heating element, wherein the processor is programmed to control operation of the induction heating element.

20. The vaporizer device of clause 19, wherein the processor is a programmed to cause the induction heating element to apply a predetermined heating profile to the vaporizable substance.

21. The vaporizer device of clause 17, wherein the cartridge comprises content information associated with the cartridge.

22. The vaporizer device of clause 21, further comprising a processor coupled to the induction heating element to control operation of the induction heating element, wherein the processor is programmed to:
read the content information of the cartridge;
cause the induction heating element to apply a predetermined heating profile to the vaporizable substance according to the content information of the cartridge.

We claim:

1. A vaporizer device comprising:
a housing;
a cartridge located within the housing and configured to hold a vaporizable substance;
a wick element located within the cartridge, wherein the wick element is configured to contact the vaporizable substance located in the cartridge, and wherein the wick element comprises a susceptor material;
an induction heating element located within the housing and inductively coupled to the wick element and not in contact with the wick element, wherein the cartridge is positioned such that the induction heating element is around at least a portion of the cartridge, and wherein the wick element is at least partially surrounded by the induction heating element, wherein the induction heating element comprises an induction coil; and
a power source electrically connected to the induction heating element;
wherein the wick element is configured to heat the vaporizable substance based on induction heating of the wick element by the induction heating element;
wherein the cartridge comprises a reservoir, and wherein the wick element is contained within the reservoir and is configured to transfer the vaporizable substance from the reservoir based on a capillary action of the wick element; and
wherein the induction heating element receives an alternating current from the power source and creates an electromagnetic induction field around the wick element, and wherein the wick element generates heat based on the electromagnetic induction field.

2. The vaporizer device of claim 1, further comprising an insulating member disposed between the wick element and the induction heating element.

3. The vaporizer device of claim 2, wherein the induction coil is disposed about the insulating member.

4. The vaporizer device of claim 3, wherein the insulating member defines an inside surface and wherein the wick element is positioned adjacent to the inside surface of the insulating member.

5. The vaporizer device of claim 1, wherein the wick element comprises a magnetic material or a metallic conductor.

6. The vaporizer device of claim 5, wherein the wick element has a material configuration, wherein the material configuration is selected from the group consisting of a mesh, a plurality of strands, a porous solid material, and any combination thereof.

7. The vaporizer device of claim 1, wherein the induction heating element is configured to heat the wick element to cause the vaporizable substance to produce a vapor for inhalation by a human being when the vaporizable substance is heated to a predetermined temperature.

8. The vaporizer device of claim 7, wherein the vaporizable substance is selected from the group consisting of a liquid, a wax, a plant material, and any combination thereof.

9. The vaporizer device of claim 1, further comprising at least one additional heating element.

10. The vaporizer device of claim 9, wherein the at least one additional heating element is a resistive heating element or another induction heating element.

11. The vaporizer device of claim 1, further comprising a processor coupled to the induction heating element, wherein the processor is configured to control operation of the induction heating element.

12. The vaporizer device of claim 11, wherein the processor is programmed to restrict operation of the induction heating element to a specific user of the vaporizer device.

13. The vaporizer device of claim 12, wherein the processor is programmed to cause the induction heating element to apply a predetermined heating profile to the vaporizable substance.

14. The vaporizer device of claim 13, wherein the predetermined heating profile is based on the vaporizable substance.

15. A vaporizer device comprising:
a housing;
a cartridge located within the housing and configured to hold a vaporizable substance;
a wick element comprising a susceptor material, wherein the wick element is contained within the cartridge, wherein the wick element is configured to contact the vaporizable substance held in the cartridge, and wherein the wick element is configured to heat the vaporizable substance based on induction heating of the wick element;
an induction heating element located within the housing not in contact with the wick element, wherein the cartridge is positioned such that the induction heating element is around at least a portion of the cartridge, and wherein the wick element is at least partially surrounded by the induction heating element, wherein the induction heating element comprises an induction coil; and
a power source coupled to the induction heating element;
wherein the induction heating element receives an alternating current from the power source and creates an electromagnetic induction field around the wick element, and wherein the wick element generates heat based on the electromagnetic induction field.

16. The vaporizer device of claim 15, further comprising a processor coupled to the induction heating element, wherein the processor is programmed to control operation of the induction heating element.

17. The vaporizer device of claim 16, wherein the processor is programmed to cause the induction heating element to apply a predetermined heating profile to the vaporizable substance.

18. The vaporizer device of claim 15, wherein the cartridge comprises content information associated with the cartridge.

19. The vaporizer device of claim 18, further comprising a processor coupled to the induction heating element to control operation of the induction heating element, wherein the processor is programmed to:
  read the content information of the cartridge;
  cause the induction heating element to apply a predetermined heating profile to the vaporizable substance according to the content information of the cartridge.

20. The vaporizer device of claim 15, wherein the vaporizable substance is selected from the group consisting of a liquid, a wax, a plant material, and any combination thereof.

21. A vaporizer device comprising:
a housing;
a cartridge located within the housing and configured to hold a vaporizable substance;
a wick element comprising a susceptor material, wherein the wick element is contained within the cartridge and wherein the wick element is configured to heat the vaporizable substance based on induction heating of the wick element;
an induction heating element located within the housing not in contact with the wick element, wherein the cartridge is positioned such that the induction heating element is around at least a portion of the cartridge; and
a power source coupled to the induction heating element; and
a valve coupled to the cartridge, wherein the valve is configured to control airflow;
wherein the cartridge comprises a reservoir, and wherein the wick element is contained within the reservoir and is configured to transfer the vaporizable substance from the reservoir based on a capillary action of the wick element; and
wherein the induction heating element receives an alternating current from the power source and creates an electromagnetic induction field around the wick element, and wherein the wick element generates heat based on the electromagnetic induction field.

* * * * *